United States Patent
Brais et al.

(10) Patent No.: US 10,857,249 B2
(45) Date of Patent: Dec. 8, 2020

(54) ROOM DECONTAMINATION APPARATUS

(71) Applicant: SANUVOX TECHNOLOGIES INC., Montreal (CA)

(72) Inventors: Normand Brais, Bosemere (CA); Benoit Despatis Paquette, Laval (CA); Jocelyn Dame, Saint-Lazare (CA)

(73) Assignee: SANUVOX TECHNOLOGIES INC., Montreal (CA)

( * ) Notice: Subject to any disclaimer, the term of this patent is extended or adjusted under 35 U.S.C. 154(b) by 0 days.

(21) Appl. No.: 15/936,604

(22) Filed: Mar. 27, 2018

(65) Prior Publication Data

US 2018/0296711 A1 Oct. 18, 2018

Related U.S. Application Data

(63) Continuation of application No. 15/118,982, filed as application No. PCT/CA2015/050388 on May 5, 2015, now Pat. No. 9,956,306.

(30) Foreign Application Priority Data

May 5, 2014 (WO) ................ PCT/CA2014/050424

(51) Int. Cl.
*A61L 2/10* (2006.01)
*H05B 47/105* (2020.01)
(Continued)

(52) U.S. Cl.
CPC ........ *A61L 2/10* (2013.01); *A61L 9/20* (2013.01); *H05B 47/105* (2020.01);
(Continued)

(58) Field of Classification Search
CPC ....................................................... A61L 2/10
See application file for complete search history.

(56) References Cited

U.S. PATENT DOCUMENTS

| 3,967,478 A | 7/1976 | Guinn |
| 4,897,630 A * | 1/1990 | Nykerk ............ B60R 25/04 340/309.16 |

(Continued)

FOREIGN PATENT DOCUMENTS

| WO | WO 01/60419 A1 | 8/2001 |
| WO | WO 2014/036080 A1 | 3/2014 |

OTHER PUBLICATIONS

International application No. PCT/CA2014/050424 Search Strategy dated Oct. 9, 2014.

(Continued)

*Primary Examiner* — Donald R Spamer
(74) *Attorney, Agent, or Firm* — Anglehart et al.

(57) ABSTRACT

A room decontamination systems, controllers and methods for decontaminating a room. The room decontamination system may be a UV room decontamination system that uses UV radiation to perform a decontamination operation in the room. A controller may determine whether safe conditions for decontamination exist and initiate a decontamination operation on the basis of whether they exist. Determination of safe conditions for decontamination may be based on light actuation detection and/or sensor data, which may include presence detector data and door sensor data. Determination of safe conditions for decontamination may include a determination of whether sensors are functioning properly. The controller may also determine whether decontamination operations are required on the basis of the historical condition data, for example on the basis of whether the room has been occupied since the last decontamination operation.

20 Claims, 15 Drawing Sheets

(51) Int. Cl.
*A61L 9/20* (2006.01)
*A61N 5/06* (2006.01)

(52) U.S. Cl.
CPC ....... *A61L 2202/14* (2013.01); *A61L 2202/25* (2013.01); *A61N 5/0624* (2013.01); *Y02B 20/44* (2013.01)

(56) References Cited

U.S. PATENT DOCUMENTS

| | | | |
|---|---|---|---|
| 5,459,322 | A | 10/1995 | Warkentin |
| 5,891,399 | A | 4/1999 | Owesen |
| 5,901,564 | A | 5/1999 | Comeau, II |
| 6,577,240 | B2 | 6/2003 | Armstrong |
| 6,823,251 | B1 * | 11/2004 | Giers ................. B60G 17/0185 303/122 |
| 6,911,177 | B2 | 6/2005 | Deal |
| 7,372,044 | B2 | 5/2008 | Ross |
| 7,490,578 | B1 | 2/2009 | Mottard |
| 7,791,044 | B1 | 9/2010 | Taylor et al. |
| 8,067,750 | B2 * | 11/2011 | Deal ........................ A61L 2/10 250/453.11 |
| 8,097,861 | B2 | 1/2012 | Leben |
| 8,178,042 | B2 | 5/2012 | Jung et al. |
| 8,551,399 | B2 | 10/2013 | Shannon et al. |
| 8,859,994 | B2 | 10/2014 | Deal |
| 2005/0276720 | A1 | 12/2005 | Correa |
| 2006/0120915 | A1 | 6/2006 | Lewandowski |
| 2012/0282135 | A1 * | 11/2012 | Trapani ..................... A61L 2/10 422/3 |
| 2012/0305787 | A1 | 12/2012 | Henson |
| 2012/0310376 | A1 * | 12/2012 | Krumm .................. G05B 15/02 700/31 |
| 2012/0313014 | A1 | 12/2012 | Stibich et al. |
| 2013/0002445 | A1 | 1/2013 | Stibich et al. |
| 2013/0062534 | A1 * | 3/2013 | Cole ......................... A61L 2/10 250/454.11 |
| 2013/0234041 | A1 | 9/2013 | Deal |
| 2014/0059796 | A1 * | 3/2014 | Boodaghians ............ A61L 2/10 15/339 |
| 2014/0060104 | A1 | 3/2014 | Shur et al. |

OTHER PUBLICATIONS

International application No. PCT/CA2014/050424 Written Opinion of the International Searching Authority dated Oct. 9, 2014.
International application No. PCT/CA2015/050388 International Search Report dated Aug. 25, 2015.
International application No. PCT/CA2015/050388 Search Strategy dated Aug. 25, 2015.
International application No. PCT/CA2015/050388 Written Opinion of the International Searching Authority dated Aug. 25, 2015.
Canadian application No. 2939722 office action dated Jan. 10, 2017.
Canadian application No. 2956524 office action dated Nov. 27, 2017.
International application No. PCT/CA2014/050424 International Preliminary Report on Patentability Chapter I dated Nov. 8, 2016.
International application No. PCT/CA2015/050388 International Preliminary Report on Patentability Chapter I dated Nov. 8, 2016.
U.S. Appl. No. 15/118,982 office action dated Jul. 3, 2017.

* cited by examiner

ROOM DECONTAMINATION APPARATUS

CROSS-REFERENCE TO RELATED APPLICATIONS

This application is a continuation of U.S. Non-Provisional Patent Application No. 15/118,982 filed on Aug. 15, 2016, now allowable, which, in turn, is a national stage entry of International Application No. PCT/CA2015/050388 filed on May 5, 2015 and designating the United States, which, in turn, claims priority to International Application No. PCT/CA2014/050424 filed on May 5, 2014 and designating the United States, the entireties of which are incorporated herein by reference.

This application claims priority of International Application No. PCT/CA2014/050424 filed on May 5, 2014.

TECHNICAL FIELD

The present invention relates to the field of decontamination and more specifically of room decontamination.

BACKGROUND

Infections are known to spread through microorganisms such as bacteria, fungi, viruses, protozoa. Such microorganism can exist in room environments in the air or on exposed surfaces. When a person comes into contact with the pathogens they are at risk of developing an infection.

Hospitals are a particular concern. Nosocomial infections are common, costly and can be lethal. While good personal hygiene such as thorough hand washing among patients, physicians, nursing staff and other hospital staff can be a very effective tool to reduce contagion, the hospital environment itself can contribute to nosocomial infections by harboring virulent strains of bacteria, fungi and viruses that can cause infections. Surface decontamination is a critically important task to prevent nosocomial infections and techniques for decontaminating vary from washing surfaces with decontaminating chemicals to fumigation with gas. Fumigation is problematic because it is time consuming and requires the use of dangerous chemicals and evacuation of the used area for a considerable amount of time. Consequently it generally cannot be performed often enough to maintain a healthy level of topical decontamination in most environments. Topical antiseptics are often used for cleaning surfaces, but this too is a time consuming task, usually involving a human cleaner, which cannot be performed often. Moreover, not all surfaces can be easily cleaned and even on those that can be, this form of decontamination is subject to human error and its effectiveness cannot easily be quantified.

Ultraviolet (UV) germicidal radiation has been successfully used in purification and sterilization systems for various media, such as air, water, and food. Ultraviolet germicidal radiation has proven effective at destroying antibiotic resistant organisms. UV radiation is a particularly useful tool in the fight against hospital acquired infections superbugs such as Clostridium Difficile (C. Diff), Methicillin Resistant Staphylococcus Aureus (MRSA), Vancomycin Resistant Enterococcus (VRE), etc.

UV decontamination systems may sterilizes the media or surface by exposing it to ultraviolet radiation of a sufficient power and for a sufficient exposure time to destroy by dimerization of thymine pairs the DNA molecular structure of bacteria, viruses, protozoa, and other organisms, which may be present in the media.

U.S. Pat. No. 5,891,399 describes a UV air purification system that comprises UV light sources in a housing which has a fan to draw air through the housing to be exposed to UV radiation. When the room the housing is in is empty, covers can open to expose some surfaces of the room to the UV radiation. An IR detector can be used to cut off possible current supply to the UV lamps when a human being or animal enters the room in question.

U.S. Pat. No. 8,097,861 describes an elevator sanitizing system which has a UV light which can be rotated in to take the place of a visible light to sanitize the elevator inner surfaces. The system features a sensor for sensing the presence of a human and a sensor for sensing the when the elevator's doors are closed.

SUMMARY

In accordance with a first non-limiting embodiment is provided a single-occupant room UV decontamination system installed in a single-occupant bathroom. The system comprises condition sensing hardware for detecting a room condition used in determining whether safe conditions for decontamination exist in the single-occupant bathroom, the condition sensing hardware comprising at least a door sensor for detecting door use. The system further comprises UV decontamination hardware for applying a decontamination operation on the single-occupant bathroom, the decontamination operation including exposing at least a portion of the single-occupant bathroom to UV radiation. The system further comprises a controller in communication with the condition sending hardware and the UV decontamination hardware, the controller being configured for initiating the decontamination operation at least in part on the basis of a determination of safe conditions, and for interrupting the decontamination operation when a door use is detected.

In accordance with another non-limiting embodiment is provided a room decontamination system controller for controlling a room decontamination system for decontaminating a room. The room decontamination system controller comprises a condition sensing hardware interface for connecting to condition sensing hardware suitable for generating sensor data, the room decontamination system controller being configured for receiving sensor data over the condition sensing hardware interface and determining, at least in part on the basis of the sensor data, whether safe conditions for decontamination exist in the room. The room decontamination system further comprises a decontamination hardware interface for connecting to interruptible decontamination hardware suitable for applying a decontamination operation on the room, the decontamination controller further being configured for controlling decontamination hardware to cause initiation of decontamination operation when safe conditions exist and for causing interruption of the decontamination operation when safe conditions cease to exist. The room decontamination system controller further comprises a logging system configured for generating decontamination operation data representative of decontamination operations initiated by the room decontamination system controller and for populating a historical decontamination operations log with the decontamination operation data. The room decontamination system controller further comprises an output configured for outputting data generated by the logging system.

In accordance with another non-limiting embodiment is provided a room decontamination system comprising condition sensing hardware for generating sensor data, interruptible decontamination hardware suitable for applying a decontamination operation on the room, a controller operatively connected to the condition sensing hardware, the interruptible decontamination hardware. The controller is configured for determining, on the basis of the sensor data whether safe conditions for decontamination exist in the room. The controller is further configured for causing initiation of decontamination operation when safe conditions exist. The controller is further configured for causing interruption of decontamination operation when safe conditions cease to exist. The controller is further configured for generating decontamination operation data representative of decontamination operations and populating a historical decontamination operations log with the decontamination operation data. The controller is further configured for outputting data generated by the logging system.

In accordance with yet another non-limiting embodiment is provided a method for applying an interruptible decontaminating operation to a room. The method comprises receiving sensor data from condition sensing hardware and determining, on the basis of the sensor data whether safe conditions for decontamination exist in the room. The method further comprises if safe conditions for decontamination exist in the room, causing the initiation by decontamination hardware of an interruptible decontamination operation on the room and causing interruption of the decontamination operation if during the decontamination operation safe conditions cease to exist. The method further comprises generating decontamination operation data representative of decontamination operation. The method further comprises storing the decontamination operation data in a historical decontamination operations log comprising decontamination operation data corresponding to more than one instance of decontamination operation. The method further comprises outputting the historical decontamination operations log.

In accordance with yet another non-limiting embodiment is provided a UV room decontamination system controller comprising a sensor interface configured for connecting to condition sensing hardware and to receive therefrom sensor data, a visible light source interface for controlling activation of a visible light source, a room decontamination hardware interface for connecting to UV decontamination hardware and for controlling initiation of a room decontamination operation, and a user input device interface configured for receiving an indication of a particular user input action at a user input device. The UV room decontamination system controller is configured for monitoring sensor data received at the sensor interface to establish a condition of possible room non-occupancy. The UV room decontamination system controller is further configured for causing the visible light source interface to deactivate the visible light source connected thereto when the condition of possible room non-occupancy is established. The UV room decontamination system controller is further configured for monitoring the user input device interface, when the condition of possible room non-occupancy is established, to establish a condition of confirmed room non-occupancy in the absence of the particular user input action. The UV room decontamination system controller is further configured for causing the initiation of a room decontamination operation when the condition of confirmed room non-occupancy is established.

In accordance with yet another non-limiting embodiment is provided a UV room decontamination system comprising condition sensing hardware for generating sensor data, a visible light source, UV room decontamination hardware, a user input device, and a controller operatively connected to the condition sensing hardware, the visible light source, the UV room decontamination hardware, and the user input device, The controller is configured for receiving the sensor data from the condition sensing hardware and establish, at least in part on the basis of the sensor data a condition of possible room non-occupancy. The controller is further configured for deactivate the visible light source when a condition of possible non-occupancy is established. The controller is further configured for monitoring the user input device, when a condition of possible room non-occupancy is established, and establishing a condition of confirmed room non-occupancy in the absence of a detection of a particular user input. The controller is further configured for initiating a room decontamination operation when the condition of confirmed room non-occupancy is established.

In accordance with yet another non-limiting embodiment is provided a retrofitable UV room decontamination system suitable for retrofitting to a room comprising a lighting system having a light actuator and a light source. The retrofitable UV room decontamination system comprises condition sensing hardware for generating sensor data, a visible light source interface for controlling activation of a visible light source, UV decontamination hardware capable of performing a UV room decontamination operation, a light actuator interface configured for detecting a user light actuation, and a controller operatively connected to the condition sensing hardware, the visible light source interface, the UV decontamination hardware, and the light actuator interface. The controller is configured for receiving the sensor data from the condition sensing hardware and establishing, at least in part on the basis of the sensor data a condition of possible room non-occupancy. The controller is further configured for causing a deactivation of the visible light source when a condition of possible non-occupancy is established. The controller is further configured for monitoring the actuator interface, when a condition of possible room non-occupancy is established, to establish a condition of confirmed room non-occupancy in the absence of a detection of a user light actuation. The controller is further configured for initiating a room decontamination operation by the UV decontamination hardware when the condition of confirmed room non-occupancy is established.

In accordance with yet another non-limiting embodiment is provided a method for safely applying a UV decontaminating operation to a room having a visible light source and an actuator for the visible light source. The method comprises monitoring sensor data generated by condition sensing hardware to establish a condition of possible room non-occupancy. The method further comprises deactivating the visible light source when a condition of possible room non-occupancy is established. The method further comprises monitoring the actuator to establishing to detect the presence of a user light actuation when a condition of possible room non-occupancy is established and, if no user light actuation is detected, establishing a condition of confirmed room non-occupancy wherein a room decontamination operation comprising the activation of a UV light source in the room is initiated; if a user light actuation is detected, determining a room occupancy condition wherein no decontamination operation is initiated.

In accordance with yet another non-limiting embodiment is provided a room UV decontamination system comprising a door sensor configured for installing in relation to a door and detecting the status of the door to generate an output indicative of the status of the door. The system further comprises a presence detector for detecting the presence of a body in proximity to the door and generating an output indicative of a detected presence. The system further comprises UV decontamination hardware suitable for applying a decontamination operation to a room, the decontamination operation including irradiating the room with UV radiation. The system further comprises a controller in communication with the door sensor, the presence detector and the UV decontamination hardware, the controller being configured for performing a determination that safe conditions exist for the decontamination operation and initiating the decontamination operation at least in part on the basis of the determination of safe conditions, wherein the determination of safe conditions comprises a confirmation that the presence detector is functioning properly.

In accordance with yet another non-limiting embodiment is provided a room UV decontamination system comprising condition sensing hardware for detecting a room condition used in determining whether safe conditions for decontamination exist in a room, the condition sensing hardware being configured for generating sensor data indicative of the room condition wherein the room. The system further comprises UV decontamination hardware suitable for applying a decontamination operation to a room, the decontamination operation including irradiating the room with UV radiation. The system further comprises a controller in communication with the condition sensing hardware for receiving the sensor data, the controller being configured for performing a determination that safe conditions exist for the decontamination operation on the basis of the sensor data and initiating the decontamination operation at least in part on the basis of the determination of safe, wherein the controller is configured for determining, on the basis of the sensor data, whether a decontamination operation is required.

In accordance with yet another non-limiting embodiment is provided a method for decontaminating a room comprising receiving output from condition sensing hardware, the condition sensing hardware comprising at least a door sensor and a presence detector, the output comprising at least door sensor output and presence detector output. The method further comprises performing a confirmation on the basis of the output from the condition sensing hardware that the presence detector is functioning properly. The method further comprises determining, on the basis of the output from the condition hardware and on the basis of the confirmation that the presence detector is functioning properly that safe conditions for decontamination exist in the room. The method further comprises at least in part in response to the determination that safe conditions for decontamination exist, initiating a decontamination operation.

BRIEF DESCRIPTION OF THE DRAWINGS

The invention will be better understood by way of the following detailed description of embodiments of the invention with reference to the appended drawings, in which.

DETAILED DESCRIPTION

Figure 1:
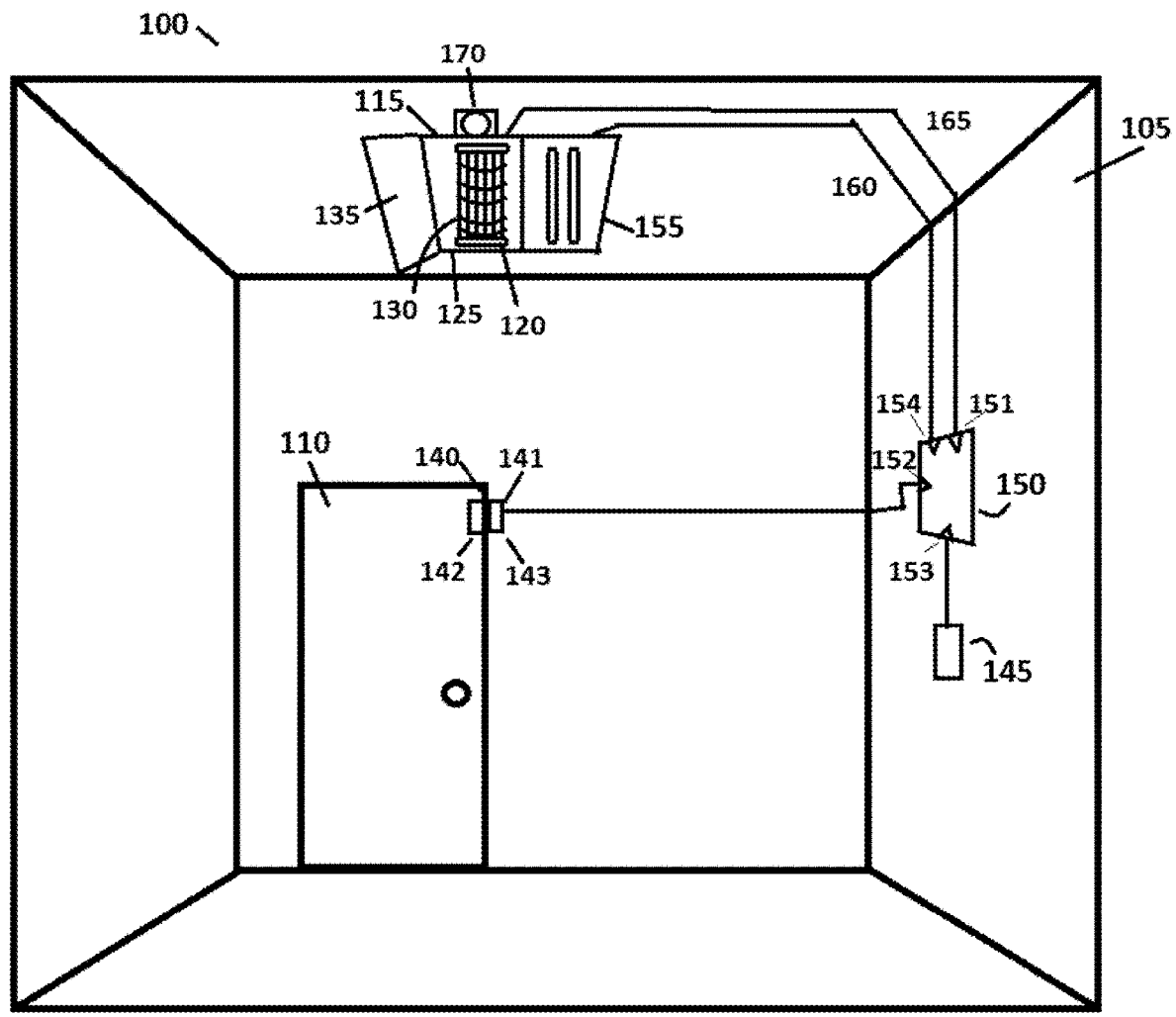
FIG. 1 is a rear view of a room in which a room decontamination system is installed according to a non-limiting embodiment.

Room decontamination poses certain challenges but is particularly important in light of the ability of infections to spread due to pathogens present on surfaces within rooms and in the air in room.

Bathrooms surfaces are particularly subject to contacting infected bodily fluids and becoming host to pathogens such as bacteria, viruses and protozoa that can cause disease. Bathrooms are used frequently and often by different people. For example, in hospitals, single-user bathrooms will often be used by several patients. Single-user rooms are rooms that are typically used by a single user at a time. In the case of bathrooms, single-user bathrooms will typically have a door at a single point of entry, and contain a toilet and a sink, although this particular configuration is not the only possible one. Single-user bathrooms are often found on hospital floors, and are often annexed to shared hospital rooms, where a shared room will have several beds for several patients but one single-user bathroom as annex. Such rooms can be difficult to keep satisfactorily decontaminated since they may be very numerous and significant cleaning staff resources are needed to clean them regularly. Moreover, being that they can be in use when the cleaning staff comes, it is not always possible to guarantee every such bathroom will be cleaned on a regular schedule.

Different terms are used to describe bathrooms in different parts of the world. Terms like lavatory or toilet are sometimes used interchangeably with the term bathroom. In some places, different terms indicate different variants of such rooms. For example according to certain local usage, bathroom may be used to refer to a room with a bath or a shower, lavatory may be used for a room with a personal sink and faucet, and a water closet may be used for a room having a toilet. However, in this description it is to be understood that bathroom is meant to encompass all those terms. Commonly, for example in North-America, any room comprising a toilet, bath, personal hygiene equipment such as a hand washing station or any combination thereof may be considered a bathroom. As such the term bathroom is not meant to be limited to any subset of its broadest definition.

Nosocomial infections are a major concern because hospitals often combine several factors that allow nosocomial infections to exist and cause maximum harm. To begin with, hospitals tend to host patients that are themselves infected by pathogenic infection and these patients may act as sources of pathogens spreading them on surfaces and in the air they come in contact with. Moreover, hospitals can be very large buildings and it can be logistically very challenging to ensure regular decontamination throughout the hospital, particularly in all individual rooms and bathrooms which have irregular occupation schedules. Also, hospitals are often host to people who are particularly vulnerable to infection for a variety of reasons. Elderly people, infants, people weakened by other medical conditions and immunocompromised patients are among some of the people most vulnerable to nosocomial infections and are readily found in hospitals.

Besides hospitals, however, other facilities are also host to people prone to spreading infection or to people that are particularly vulnerable to pathogenic infections. Nursing homes for the elderly, infant nurseries, homeless shelter, addiction or rehab centers and prisons are all places where vulnerable or immunocompromised persons may be found. These facilities tend to have a responsibility towards the persons they host and therefore must take particular care in preventing the spread of infections within them.

Herein is provided a room decontamination system that can decontaminate room to reduce or eliminate the risk of pathogenic infections. For the purpose of providing an example, the room will be assumed to be a bathroom, and more particularly a single-user bathroom in a hospital. Indeed the system described herein is particularly well suited for decontaminating such rooms. A skilled person, however, will appreciate that the system described can be employed in other types of room. A room is generally an enclosed space that can be occupied by a living being. Typically a room will have at least one entrance point in the form of a suitable opening in the enclosure. The entrance point will typically have a door, which is a mechanism for selectively blocking the opening. Typical doors may be hinged or sliding doors, but other door types are possible.

The room decontamination system employs decontamination hardware. In one particular embodiment, a system for decontaminating a room using ultraviolet (UV) radiation is provided. In one embodiment, ultraviolet radiation having wavelength(s) close to the absorption peaks of biologically significant molecules of deoxyribonucleic acid (DNA) and proteins can be used.

Typically, the source of the ultraviolet radiation in an ultraviolet decontamination system is a mercury lamp. To this extent, a low-pressure or a medium-pressure mercury lamp provides a spectrum of radiation with one or more peak lines having a wavelength that is in the relative vicinity to the DNA absorption line. For example, a low-pressure mercury lamp having a main peak at 254.7 nanometers (nm) is may be used in low-consumption residential water purification systems and residential air purification systems.

When UV radiation or other harmful decontamination methods are used to decontaminate a room, it is important to ensure that the room is unoccupied nobody is in the room since UV radiation can be harmful to humans and other living beings. Generally, room occupancy entails the presence of a human in the room, but it may be desirable to ensure that the room is not occupied by other animals that are also vulnerable to UV radiation. Ensuring non-occupancy causes a challenge. Past solution have involved carting UV room decontamination units into room and blocking access to the room during decontamination. This is problematic because it is both labor intensive and renders the room unusable. For many rooms, particularly bathrooms, blocking access to the room is undesirable because people may have urgent needs to use the bathroom. One solution provided herein is to provide an interruptible decontamination system that conducts decontamination when possible but can readily be interrupted to use the room. This allows the room to be kept unlocked during operation, and if the system operates autonomously, this can also allow the system to ensure decontamination does occur, whenever it is possible, without requiring staff intervention.

An interruptible system, however poses its own challenge. If the system were uninterruptible, it would be possible to ensure a certain regularity of decontamination according to requirements such as hygienic standards. But if the system is liable to be interrupted at any time, there is no way for the operators of the facilities where it is used in to know whether it is operating often enough to ensure adequate decontamination and/or adherence to hygienic standards. For a variety of purposes, it may be desirable or required to be able to demonstrate that the system decontaminates adequately the room. For one, this may be simply necessary for facilities operators to ensure proper hygiene is observed, but it may also be required in certain instances for insurance or compliance purposes. Additionally, it may be a selling point of some facilities to be able to show a rigorous decontamination standard is applied in their rooms. Also for someone considering purchasing such a system, demonstrability of effectiveness can provide an assurance that the investment is well invested, and this data can be used to determine whether to include the system elsewhere. Additionally decontamination system providers can use the information as proof of the effectiveness of their product, which allows them to differentiate themselves over other products and allows their customers to make more informed choices.

In accordance with a first exemplary embodiment, a room decontamination system 100 is provided. The decontamination system 100 is suitable to apply a decontamination operation to a room 105. During a room decontamination operation, the room 105, or a portion thereof, is decontaminated to kill or otherwise incapacitate pathogens therein.

The decontamination system comprises decontamination hardware 115, condition sensing hardware 140, a user input device 145 and a room decontamination system controller 150. The decontamination system also comprises a visible light source 155, which may be an ordinary light source under control of the controller 150.

The controller 150 is connected to the decontamination hardware 115 by a decontamination hardware interface 151. The controller 150 is connected to the condition sensing hardware 140 by a sensor interface 152. The controller 150 is connected to the user input device 145 by the user input device interface 153. The controller 150 is connected to the visible light source 155 by the visible light source interface 154. In this particular exemplary embodiment, the controller 150 is located apart from the decontamination hardware 115, the condition sensing hardware 140, the visible light source 155 and the user input device 145. The controller 150 is connected to these via the respective interfaces and suitable circuitry such as wires.

The decontamination hardware 115 is suitable for applying the decontamination operation. In this example, the decontamination hardware 115 is UV decontamination hardware, making this room decontamination system 100 a UV room decontamination system. The UV decontamination hardware 115 may comprise any suitable UV light source as UV radiating equipment; in this example, the UV decontamination hardware 115 comprises a UV lamp 120. The UV decontamination hardware 115 also comprises a casing 125 for the UV lamp 120. The casing 125 may include a protective barrier 130, such as a metal grid, to protect the metal UV lamp 120 from accidental impact and/or to prevent injury by the inadvertent touching of the UV lamp 120 when it is hot. The UV decontamination hardware 115 may also include one or more reflective surface 135, in this case part of the casing 125, to reflect and/or redirect UV radiation emitted by the UV lamp 120.

The reader will understand that UV lamp 120 may include a replaceable UV source, like fluorescent tube, however such a replaceable UV source may also be excluded from the UV lamp. For example, if the UV lamp 120 does use replaceable UV light source(s), it will be understood that the replaceable UV light source(s) need not be provided with the lamp itself. A UV lamp may be without a UV light source if it is a UV lamp made for receiving a replaceable UV light source and is provided without one. Replaceable UV light source, e.g. UV fluorescent tubes, can be trivially purchased separately if the UV lamp is provided without tube(s) or if the UV lamp should be temporarily without tube(s).

Figure 6:
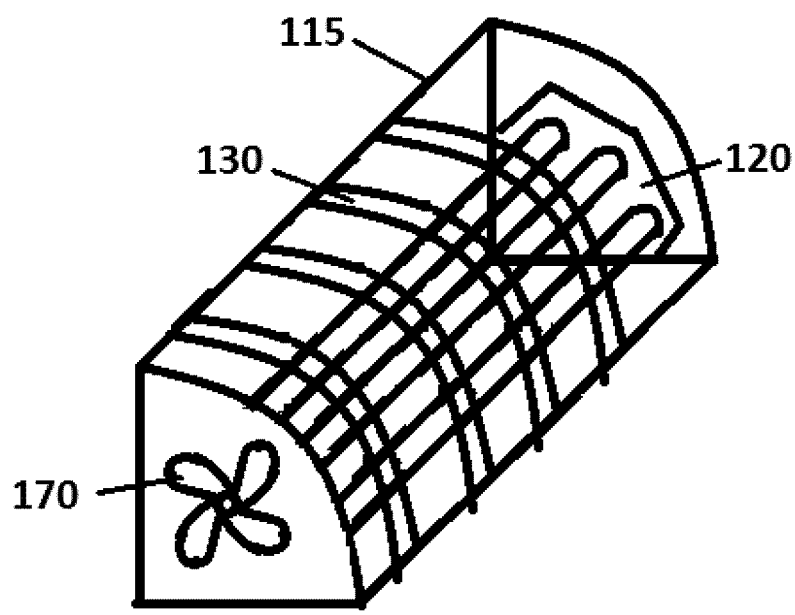
FIG. 6 is a perspective view of UV room decontamination hardware according to a non-limiting embodiment.

In this example where the decontamination hardware 115 is UV decontamination hardware, the decontamination hardware also includes a ventilation system 170 for cooling the UV lamp 120. UV light sources tend to heat and may require cooling. FIG. 6 shows an example of decontamination hardware which in this example is a UV decontamination hardware. A ventilation system 170 causes airflow over the UV lamp and more specifically over the UV light sources. In this case a low-pressure mercury lamp is used. The airflow serves a dual purpose of cooling the lamp and causing ambient air to be circulated in proximity to the UV light source to receive maximum UV light exposure and so decontaminate the air from pathogens that may be present in it. Optionally, the ventilation system 170 may be configured to draw in air and/or expel air in such a manner as to encourage full-room air circulation and ensure full decontamination of the air.

In this example, decontamination hardware 115 is interruptible, meaning that it can interrupt decontamination operations mid-operation. UV decontamination operations can easily be interrupted by cutting power to the UV lamp 120 or otherwise causing the UV decontamination hardware to stop generating UV light. As described further herein, the controller 150 is capable of controlling the decontamination hardware 115 to cause decontamination operations to take place and, in this example, to interrupt them if necessary.

Visible light source 155 can be any suitable means of providing the rooms with visible light. In this embodiment, the visible light source 155 comprises a typical ceiling-mounted neon room lighting system, although it will be appreciated that any other suitable lighting system may be used. In one example, the visible light source 155 is controlled by the controller 150 and can be activated or deactivated by the controller 150.

The user input device 145 is a device capable of receiving a user input action. For example, the user input device 145 may be a button, a switch or a pull string, although more complex examples are possible. For example, the user input device may contain a plurality of buttons for receiving a range of different possible user input actions. In the main example herein, the user input device 145 is a light actuator 145 configured for receiving a user light actuation. The user input device interface 153 in this example is a light actuator interface 153 configured for detecting the user light actuation. Throughout this description, the user input device will be provided in exemplary form as a light actuator 145 (e.g. a push-button), however it is to be understood that other embodiments are possible. As described herein, the user input device serves to determine that the room 105 is occupied. When someone is in the room 105, providing a particular user input action at the user input device allows the controller 150 to determine room occupancy. More particularly in one example the user input device is configured for receiving an indication of a particular user input action at a user input device and the controller 150 is configured for monitoring the user input device interface, when the condition of possible room non-occupancy is established, to establish a condition of confirmed room non-occupancy in the absence of the particular user input action. The controller 150 may also be configured for when monitoring the user input device interface, determining room occupancy of the room upon detecting the particular user input action.

Before turning to the main example wherein the user input device is a light actuator 145, some examples of other embodiments should be considered. As will be described, the light actuator 145 is used to determine someone is in the room because the controller 150 deactivates the visible lights when it has established that there is possibly no one in the room. The room obscurity creates a situation where a user needs or likely wants to manifest his/her presence by actuating the lights. However, the user input device may be a separate input device, e.g. a button that is not a light actuator and that is separate from any light actuator present. For example, there may be a "cancel decontamination" button placed in the room 105 (alongside a light actuator if one is used, although in this case the light actuator is not necessarily used, e.g. if the lights are always on). Instead of deactivating the visible lights 155, the controller 150 may cause another situation that will compel any user to manifest his/her presence by providing a particular user input at the user input device. For example, the controller 150 may cause a loud repetitive warning/instruction to play asking any occupant to press a button.

In the main embodiment, the user input device is a light actuator and may have only one input possible. However, in other embodiments the user input device may have multiple possible inputs, for example if the user input device comprises and array of different buttons. In such a case, the particular user input may be one or more of the possible inputs. For example, in one embodiment, there are plural buttons in the user input device, but pressing only one will be considered the particular user input action. Alternatively, in a more complex device, such as a computer with a touch screen perhaps a series of GUI navigation actions, not necessarily the same at every occasion (e.g. depending on where in the GUI you start from) may be the particular user input action. Alternatively still in an example where the user input device has several buttons, pressing any one may be considered the particular user input action which allows the controller to determine room occupancy.

Light actuator 145 is a device for user actuation of the lights. An example of a light actuator is a typical light switch which opens and closes an electrical circuit feeding a light selectively based on a user input such as the toggling of a toggle switch. Any suitable actuator capable of receiving a user light actuation may be used. In this example, the light actuator 145 is a button actuator connected to the controller

150. The button on the light actuator of this example lights up when the visible lights are off and brightly displays an invitation to actuate the lights, such as a lit-up "lights" sign or a back-lit "press here" sign or a pictorial invitation to press the button. When the button is pressed, a signal indicative of the user light actuation is sent to the controller which allows the controller to detect the user light actuation.

Condition sensing hardware 140, is sensing hardware that generates sensor data which from which a certain condition is ascertained. The condition sensing hardware 140 may comprise one or more sensor of one or more types. Sensor data is used by the controller 150 to determine whether safe conditions for decontamination exist within the room 105.

In this particular example, the sensing hardware comprises a single sensor, door sensor 141. The door sensor 141 is capable of detecting door use, when a user of the door uses the door, and to generate sensor data indicative of the door use. To this effect, the door sensor 141 may detect door opening or closing or both, and generate sensor data indicative of the detected action. In the example shown here, door sensor 141 is a magnetic contact switch with a reed 143 and a magnet 142. Sensor data is generated in the form of a circuit that is closed when the magnet 142 is adjacent the reed 143. As soon as the door is opened, the circuit is opened which indicates to the controller 150 that the door is no longer shut. Advantageously, any tampering of the door sensor 141, such as by removing the magnet 142 or cutting the connecting wire will cause an open circuit, indicative of an open door, which in the case of UV decontamination is an example of an unsafe condition for decontamination since while the door is open harmful UV radiation can radiate out of the room.

The sensor hardware 140 described here is exemplary only. It will be appreciated that a number of different arrangements can be used. In terms of door sensors alone, a number of other options are possible, some better adapted to different types of doors. It is also not necessary for there to be only a single sensor. Even in terms of door sensors, additional, e.g. redundant, sensors may be used. Moreover, as will be discussed herein, other types of sensors may be used instead of, or on top of, door sensors.

In the present example, there is only one door to the room 105. It will be understood however, that in other examples, there may be multiple doors to a room. Preferably, when door sensors are used as condition sensing hardware, they may be provided on all the doors to the room 105. In certain embodiments where other sensors (e.g. motion sensors) are used, it may be possible to combine sensor use to ensure that safe conditions can be ascertained even if not all doors have door sensors, however, it is generally desirable to interrupt decontamination immediately upon the opening of any door, particularly if UV decontamination is used and in one very useful embodiment, the sensor hardware comprises door sensors for all the doors to a room. In one such example, detection of a door use at a single door is treated like a detection of a door use at door 110 in the example of FIG. 1.

As mentioned above, the condition sensing hardware 140 generates sensor data that is used by the controller 150 to determine whether safe conditions for decontamination exist. In this exemplary embodiment, safe conditions are conditions of non-occupancy of the room. The controller 150 uses the sensor data and light actuation detection in determining whether or not the room is occupied. The sensor data may vary in complexity depending on the sensor hardware used. In the example provided above, the sensor merely opens or closes a circuit depending on whether the door is shut or not. In this case, sensor data is simple; it is merely the open or closed circuit itself, which can be viewed as a Boolean datum. In this case, the sensor interface 152 may simply be a pair of connectors for connecting wiring to and from the door sensor 141. The controller 150 can monitor sensor data by verifying whether there is an open or closed circuit at the connectors.

In other embodiments, sensors may provide the controller 150 with digital data which may be representative of a Boolean state (e.g. "detection" or "no detection") or which may provide far more information on what is detected by the sensor (e.g. information on detected movement, or on detected temperature sources). In such embodiments, the sensor interface 152 is a digital interface suitable for communicating with the sensor hardware and the controller 150 comprises logic configured for analyzing the sensor data and determining whether based thereon whether to consider that the sensor has "detected" that which it is meant to detect (e.g. analyze heat source data and determine whether the sensor data indicates the presence of a human in the room). Of course, even with relatively complex sensor hardware, the detection intelligence can be provided on the sensor hardware itself, leaving the communication between the sensor hardware 140 and the controller 150 to a simple Boolean "detected" or "not detected" signal like with our door sensor example.

Figure 2:
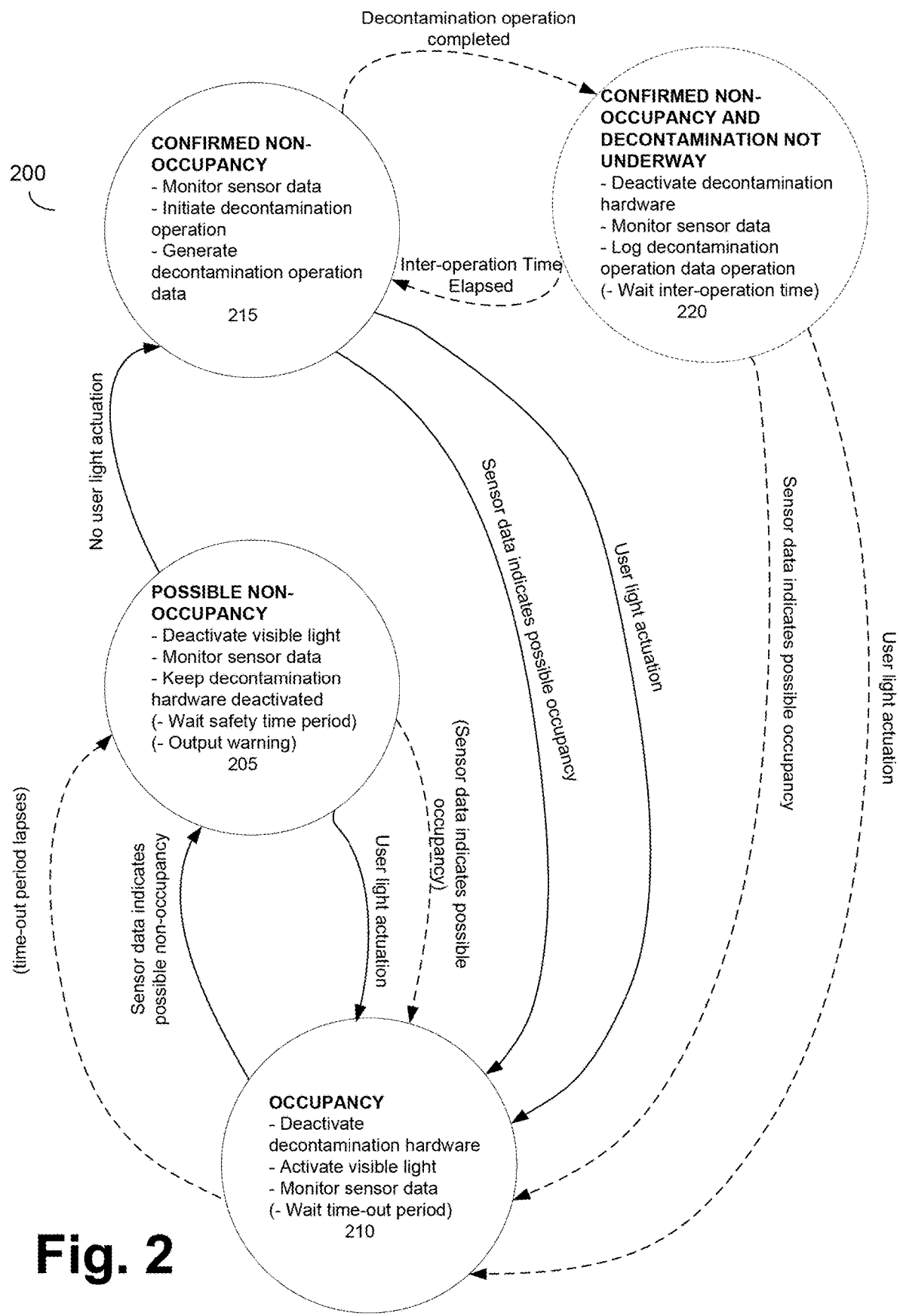
FIG. 2 is state transition diagram illustrating operation of a room decontamination system controller for the system shown in FIG. 1.

FIG. 2 is a state transition diagram indicating an exemplary operation 200 of the controller 150. As shown, the controller 150 can establish a condition of possible room non-occupancy 205. The controller 150 can determine a condition of room occupancy 210. The controller can also establish a condition of confirmed room non-occupancy 215. Optionally, the controller 150 may also be configured to determine a condition of confirmed room non-occupancy with decontamination completed 220.

Examples of operation will now be described with reference to FIGS. 3-5. It is to be noted that while these figures depict a sequence of event, they are not necessarily to chronological scale.

Figure 3:
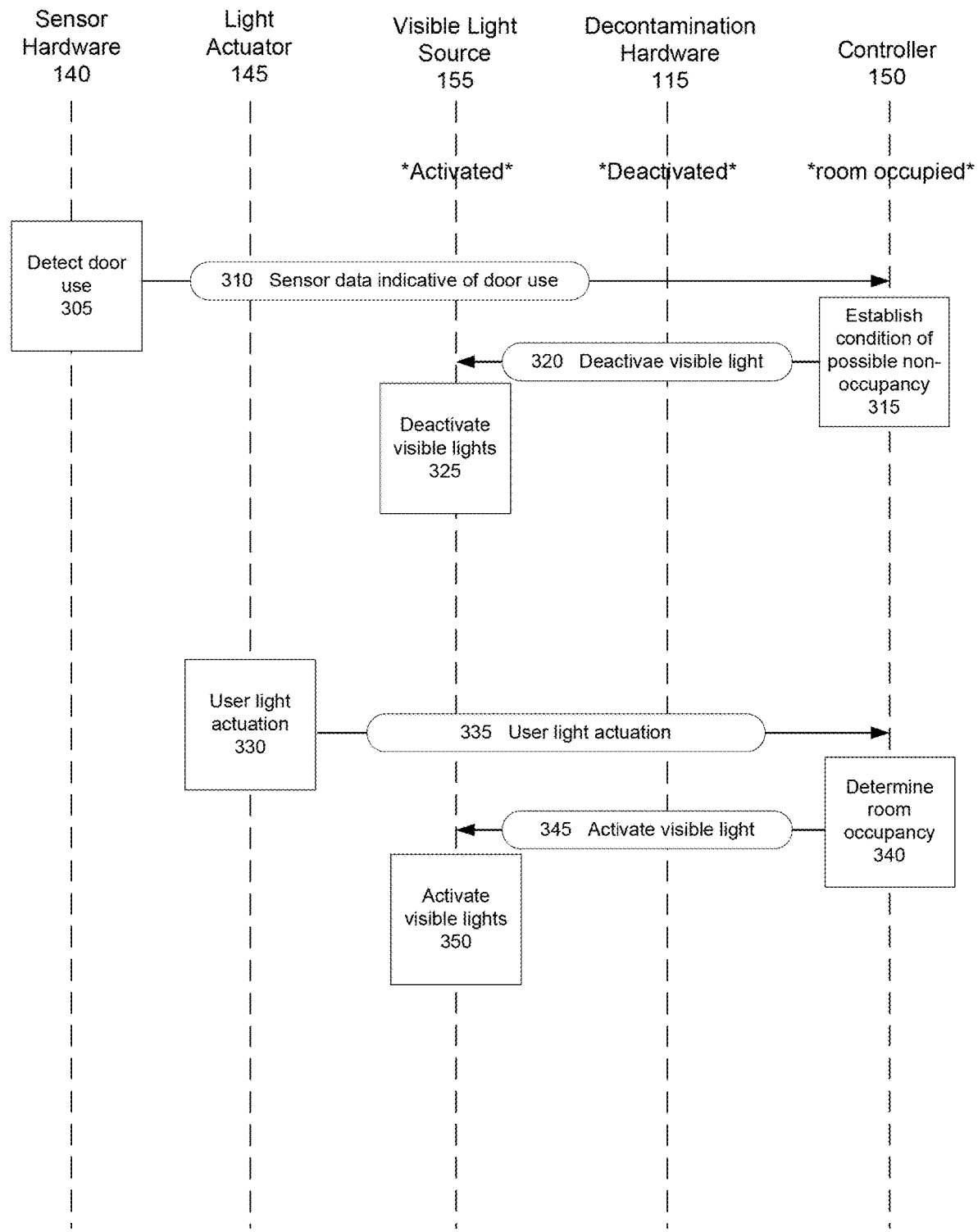
FIG. 3 is an event flow diagram illustrating the operation of the room decontamination system controller for the system shown in FIG. 1 according to a particular example.
Figure 4:
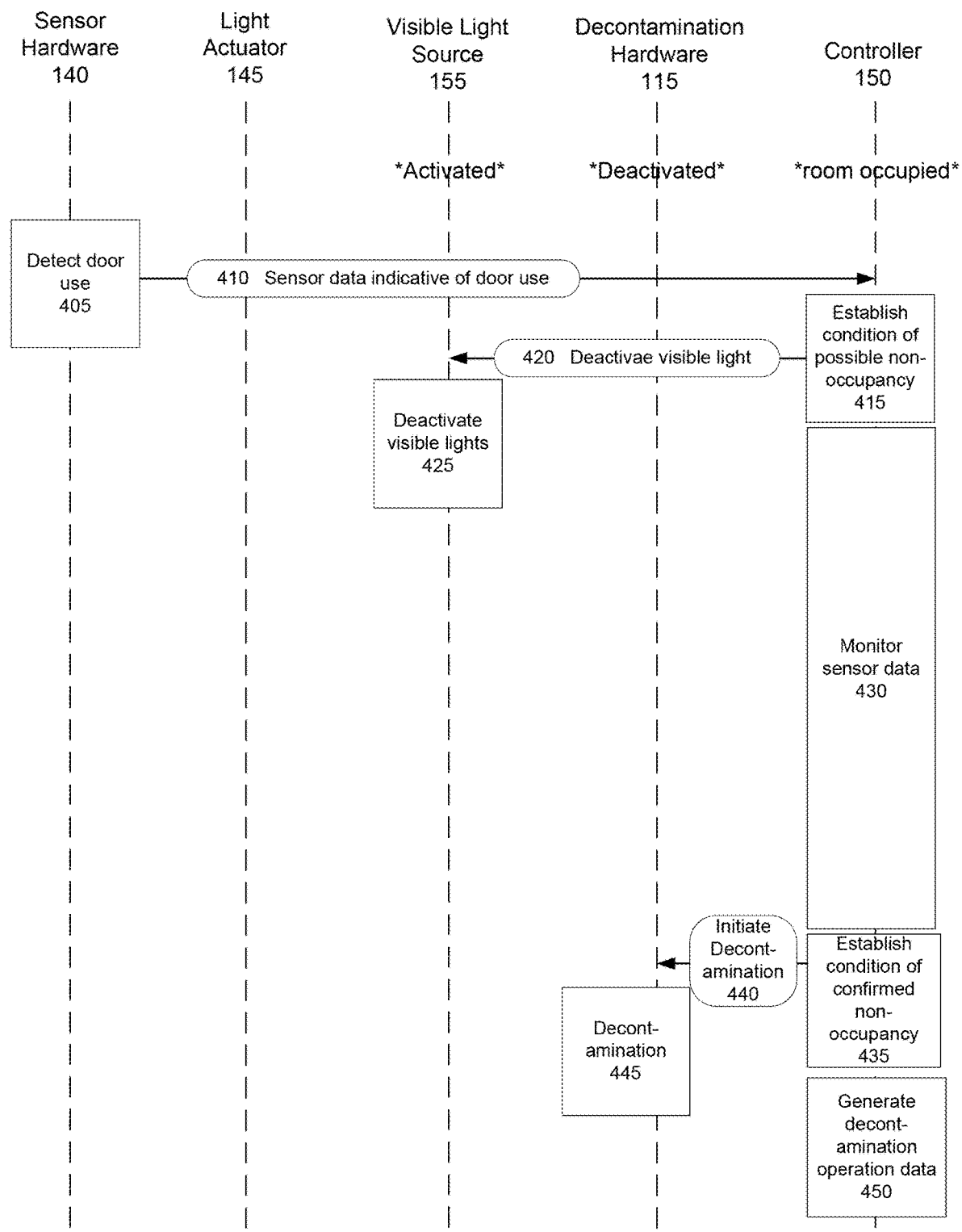
FIG. 4 is an event flow diagram illustrating the operation of the room decontamination system controller for the system shown in FIG. 1 according to another particular example.
Figure 5:
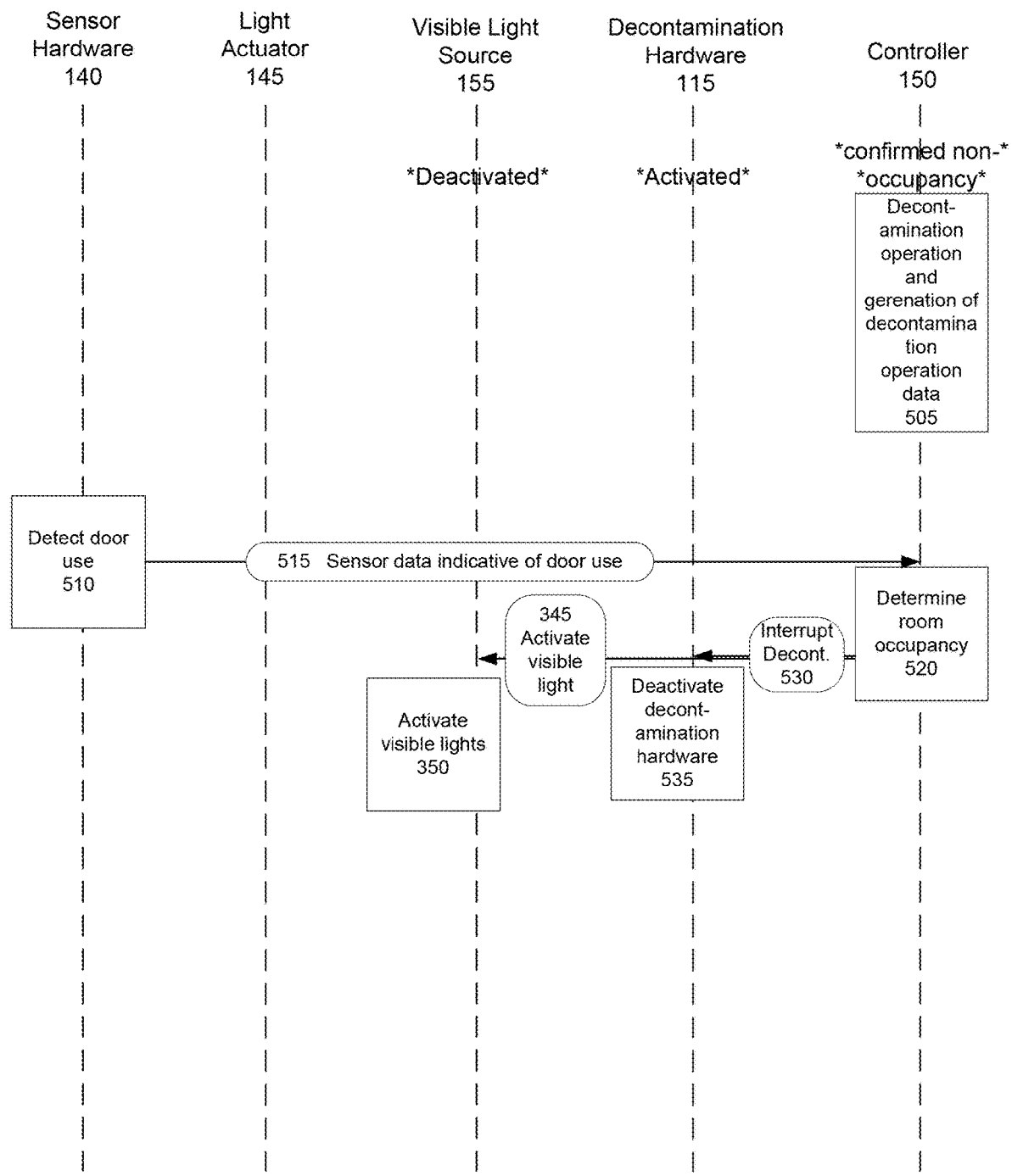
FIG. 5 is an event flow diagram illustrating the operation of the room decontamination system controller for the system shown in FIG. 1 according to yet another particular example.

While in the examples shown in FIGS. 3-5, the condition sensing hardware 140 is a door sensor 141 and the condition being detected by the condition sensing hardware 140 is a door use, it will be understood that other conditions suitable for establishing a condition of possible room non-occupancy may be detected by any condition sensing hardware suited to the task.

That being said, it has been found that door sensing is particularly useful in several scenarios where other types of condition sensing hardware are not very suitable. For example, in rooms where motion detectors cannot obtain complete coverage (e.g. in bathrooms containing several stalls) or are subject to be tricked by other non-human and non-animal motion (e.g. ventilators) door monitoring can provide an effective alternative. Door sensors also have the advantage of being inexpensive and easy to install. As mentioned above, door sensors can also be tamper-safe, for example by detecting an open door whenever any part of the sensor system isn't working. For these reasons, door sensors are particularly advantageous as a condition sensing hardware, particularly when the system 100 is to be installed in a large number of rooms, such as in hospital bathrooms.

Unfortunately door monitoring alone may not be considered sufficiently safe for determining safe conditions for a dangerous operation such as UV-based decontamination. However thanks to the techniques provided herein door monitoring can safely be used. Indeed thanks to the extra safety measures provided by controller 150, UV decontamination systems can now be safely installed in rooms without expensive and complex detecting hardware, and operated with a greater safety margin than would be obtained with, e.g. a simple motion sensor. Indeed where motion sensors alone are used to detect occupancy, a false detection of room non-occupancy could occur if a person where immobile for long enough (e.g. asleep) or if they were in an area not covered by the motion sensor. In this example therefore, the sensing hardware 140 consists of door sensor 141 and provides a remarkably suitable solution.

Turning now to FIG. 3, when the room 105 is occupied and the controller 150 has determined a condition of room occupancy 210, the controller typically causes the visible light source 155 to be activated and the decontamination hardware 115 is kept deactivated. In this state, the controller 150 monitors sensor data. In this particular example, the controller 150 observes the connectors of the sensor interface 152 to identify whether the door sensor 141 causes an open circuit. Monitoring can be performed in any suitable manner. In this particular example it does so by regularly checking the sensor interface, but in other embodiments an interrupt-based or other system can be used.

At step 305, the sensor hardware 140 detects a door use. In response to the detection, the sensor hardware 140 generates sensor data 310 indicative of the door use. In this example, the door sensor 141 causes an open circuit which is detected at the sensor interface 152 by the controller 150. The controller 150 is configured to analyze the sensor data 310 and to make conclusions as to the occupancy of the room. In this case the room 105 is a single-user bathroom, which was presumed to be occupied. The sensor data 310 indicative of a door use is interpreted by the controller 150 as indicating that the occupant has possibly left and that the room 105 may be empty. Based at least in part on the sensor data 310, the controller 150 at step 315 establishes a condition of possible room non-occupancy 205.

In this embodiment, the condition of possible room non-occupancy is a condition in which in the absence of a user action, in this example a light actuation, a condition of confirmed non-occupancy will be established, which in this example is a condition wherein decontamination is initiated. Thus in this example, the condition of possible room non-occupancy is a condition wherein if the light isn't actuated by an occupant in the room 105, a decontamination operation will begin.

When the controller 150 establishes a condition of possible room non-occupancy 205, the controller 150 does not yet initiate a decontamination operation because it is not yet confirmed that the room is not occupied. In order to confirm non-occupancy, the controller 105 causes the visible lights source 155 to be deactivated via communication 320. In response, the visible light source 155 deactivates at step 325 and ceases to illuminate the room, causing it to darken. Advantageously, this may ensure that energy is not uselessly wasted illuminating an empty room. Moreover, by automatically shutting off the lights, the user does not need to use his hands to deactivate the lights, providing one less occasion for infection propagation. To do this, the controller, may use any suitable means. In this example, visible light source 155 is connected to the controller 150 by its power cables 160, the controller 150 controlling whether or not power is provided to the visible light source 155. In this example the visible light source interface 154 may simply be a pair of terminals connected to the power cables 160 of the visible light source 155 to which the controller 150 can selectively provide power. Thus the controller 150 may communicate through the visible light source interface 154 with the visible light source 155 to cause it to selectively activate or deactivate simply by selectively providing it power.

It is to be understood that in alternate embodiments, the controller 150 may be configured to communicate differently with the visible light source 155. For example, the controller 150 may be configured to provide varying amounts of power to a dimmable light source in order to cause different levels of brightness to occur. Alternatively the controller 150 may be configured to selectively provide power to different visible lights in the visible light source 155 to achieve different levels of brightness or different areas of illumination. For this last example, it must be understood that while the visible light source 155 is shown in FIG. 1 as being unitary, it could also feature several light sources or lamps distributed in different locations in the room 105. Finally, the controller could also be configured to communicate with the visible light source 155 to provide commands for instructing the visible light source 155, or an entity controlling it, to cause the visible light source to activate or deactivate. In such a case, the controller 150 may send digital signals over a suitable digital visible light source interface.

In one particular embodiment the UV room decontamination system controller is configured to deactivate the visible light source whenever door use is detected. In this embodiment, any time someone enters the room 105, the lights will be obscured as a result of the door being opened. The first thing a user will therefore have to do is to actuate the lights. Preferably, the light actuator 145 is a big glowing button. Every time the user actuates the light, the controller 150 determines room occupancy, therefore in this embodiment, provided that users actuate the light whenever they use the room 105, room occupancy is always accurately detected. Moreover, in this embodiment, the controller 150 may establish a condition of possible non-occupancy every time the sensor data indicates door use, a condition of non-occupancy should never go undetected or mistaken for a condition of room occupancy. This embodiment works particularly well if the room is obscure when the visible light source is deactivated. For this reason, any suitable obscuring system may be used. In many cases, none will be needed as many rooms such as bathrooms have no windows to let light in. But where necessary it may be useful to provide systems for preventing light from outside of the room 105 from illuminating the room 105 sufficiently for use, e.g. by providing doors without windows, or by blocking the windows.

If someone is in the room 105 when it is darkened, they will naturally respond by actuating the light actuator 145 to turn the lights back on. To encourage this, the controller 150 may optionally be configured for outputting a warning to any room occupants. The warning may be indicative of actions required in order to prevent a decontamination operation to be initiated, or it may simply be an invitation to actuate the light actuator 145. For example, the light actuator 145 may include a glowing (e.g. lit-up) warning or invitation, which the controller 150 causes to activate. In this example, the light actuator is a button which has a light in it and a light-up indicator saying "press for light" along with a pictorial representation of that invitation, e.g. in the form of a light bulb. When the controller 150 deactivates the visible light source 155, the actuator also outputs power to the actuator light to cause it to light up the invitation. Of course, the actuator light could alternatively be kept on at all time, but simply becoming more prominent when the visible light source 155 is deactivated and the room is obscured. Other means of making the light actuator 145 glow are possible such as use of phosphorescent material in the actuator. Also, in some embodiments, the warning/invitation may simply by the glowing of the actuator 145 itself. When the visible light source is deactivated and the room 105 is obscured, a single glowing actuator is inviting to a user and beckons its actuation. Thus the light actuation 145 may be caused to glow when the visible light source is deactivated. By this it is not meant that it may not also glow when the visible light source is activated. In some embodiments it may be simplest to let whatever mechanism causes the glow (e.g. a light source within the actuator) to operate all the time. In other embodiments, it will only be activated when the room is obscured.

The controller 150 may also be configured to output other forms of warning, for example an audio warning instructing any occupant to actuate the lights or exit the room before the decontamination operation commences. To this end, the room decontamination system 100 may also comprise one or more speakers connected to the controller 150 via a speaker interface. Optionally, the output controller 150 may cause a klaxon or similar stern warning signal to blare out shortly before commencing any room decontamination operation.

During the condition of possible room non-occupancy 205, the controller 150 preferably continues to monitor sensor data, to determine room occupancy based on the sensor data if sensor data indicative of room occupancy is received. In this example, if the door sensor 141 detects use of the door 110 when condition of possible room non-occupancy 205 is established, the controller 150 determines a condition room occupancy 210. In an alternate embodiment, the controller 150 may stop monitoring sensor data after deactivating the visible light source 155, and maintain visible light source 155 deactivated regardless of door operation, determining room occupancy only if the a user light actuation is detected.

The controller 150 may be configured for waiting a safety time period prior to establishing a condition of confirmed room non-occupancy 215. This can ensure that any occupants have sufficient time to actuate the lights prior to initiation of a decontamination operation. The safety time period may also be used to ensure occupants have enough time to exit the room or otherwise manifest their presence to the controller 150 if they are still present. For example, if sensor hardware 140 comprises motion sensors, the safety time period may be made longer than normal human periods of motionlessness to ensure that the controller has not mistaken a user's immobility for an absence. This is particularly useful when certain parts of the room 105 are not covered by motion sensor coverage, such as when bathroom stalls that block motion sensor coverage are present in the bathroom. In such a case the safety time period may be of a longer duration than the time it takes for the longest reasonable bathroom stall use. In such a case, it may also be useful to ensure that there is at least on light actuator 145 in each bathroom stall, within reach of a user of the bathroom stall, to allow the user to manifest its presence without leaving the stall. If multiple light actuators are provided, actuation of a single one is sufficient to determine room occupancy.

The safety time period may be fixed. In a non-limiting example, the safety time period is fixed at 15 minutes. In other examples, the safety time period may be variable, depending on factors computed by the controller 150 or inputs to the controller 150. During the safety time period, the warnings and invitations described above may be output by the controller 150.

Returning to FIG. 3, in this example, a user is still present in the room 105 after the detected door use 305. This may happen, for example, when one user exits holding the door for another user entering the bathroom. Upon the deactivation of the visible lights 145, the occupant locates the brightly-lit light actuator 145 button and actuates it. The light actuator 145 receives the user actuation at step 330. In response, the light actuator sends a signal indicative of the user actuation to the controller 150 which receives it via the light actuator interface 153. Any suitable light actuator/signal/interface arrangement can be used. In this example, the light actuator is a simple button-type actuator. Pushing the button causes the signal indicative of the user actuation 335 to be sent, which can be a pulse along a wire connection to the controller 150 or the closing or opening of a circuit, or any other communication. Other actuator arrangements can be used as well.

The controller monitors the actuator interface 153 during condition of possible room non-occupancy 205. Like with the sensor data monitoring, the controller 150 can monitor the actuator interface 153 actively or passively. In this example, the controller 150 observes the connectors of the light actuator interface 154 to detect signal indicative of the user actuation when it is received. Monitoring can be performed in any suitable manner. In this particular example it does so by regularly checking the sensor interface, but in other embodiments an interrupt-based or other system can be used.

When the controller 150 receives the signal indicative of a user actuation 335, it detects the user light actuation and determines, on this basis a condition of room occupancy 210 at step 340.

In response to determining the condition of room occupancy 210, the controller 150 causes the activation of the visible light source 155. If a decontamination operation is in progress, the controller 150 immediately interrupts it, however in this case the controller had previously established a condition of possible (not confirmed) room non-occupancy so the decontamination hardware 115 was not activate. When the condition of room occupancy 210 is determined, the controller monitors sensor data in this example, since a detected use of the door in this state will be indicative of the possible non-occupancy of the room 105.

Optionally, when the controller 150 has determined a condition of room occupancy 210, it may count time-out period after which, if sensor data does not indicate a change in occupancy, and/or the controller 150 does not detect a light actuation the controller 150 establishes a condition of possible room non-occupancy. This can be useful to prevent prolonged periods without decontamination if the condition of occupancy was determined in error. The time-out period can be of a duration chosen such that it would be unlikely that a person would occupy the room 105 for the entire time-out period without using the door to exit. For example, the time-out period may be one hour. In the same way as the safety time period, the time-out period may be variable of fixed. At the end of the time-out period, the controller 150 establishes a condition of possible non-occupancy 205.

When conditions of room occupancy 210 are determined by controller 150, the controller is monitoring sensor data, as described above, to detect conditions of possible room non-occupancy.

Turning now to FIG. 4, when a condition of room occupancy 210 is determined and somebody comes into the room 105 using the door, the door sensor 141 detects the door use at step 405. In response, the door sensor 141 transmits sensor data 410 to the controller 150 indicative of the detection of a door use. It is to be understood that although sending the sensor data is shown here as a discrete signal 410, this is merely for the purposes of illustrating an example and does not represent a necessary constraint. Indeed, condition sensing hardware 140 may be in constant communication with controller 150 providing sensor data (e.g. such as the openness or closedness of the circuit as described above) or may otherwise communicate in other manners with the controller. As such, it is not necessary for the condition sensing hardware 140 to transmit a single discrete signal to the controller 150 when a particular condition (e.g. door use) is detected. Any manner of providing sensor data may be used.

Upon receiving sensor data indicating door use 410, the controller 150 establishes a condition of possible room non-occupancy as described above in the example pertaining to FIG. 3. Like in that example, the controller 150 causes the visible light source 155 to deactivate at step 425 via communication 420. So far, there is no difference between this and steps 305-325 of the example pertaining to FIG. 3. However in this example, nobody comes into the room 105. Thus controller 150 monitors sensor data at step 430 and receives no sensor data indicative of a door use. In this particular example, the controller 150 waits a pre-determined safety time period. In this example, the safety time period is 30 minutes, although this is just one of many possible examples. In order to wait 30 minutes, the controller 150 comprises a timer or a timing circuit, which counts out 30 minutes.

Once the timer has counter out the safety time period, if no user light actuation has been detected, the controller 150 establishes a condition of confirmed room non-occupancy 215. In this example, the controller also watches for sensor data indicating a condition of possible room occupancy. The occurrence of a light actuation or door use during the safety period would have prevented the controller 150 from establishing a condition of confirmed room occupancy 215, and caused it to determine a condition of occupancy 210.

In this example, optionally, a detected door use during a condition of possible room non-occupancy is interpreted as someone having entered the room 105 and therefore occupancy is assumed. However, this could also be due to someone walking out of the room 105 instead of turning on the lights. This leads to a falsely determined condition of occupancy. This is not critical, as false positives are far less harmful than false negatives in this system. If the room is falsely assumed to be occupied, this will simply delay the next decontamination. However, if the room were falsely confirmed to be unoccupied, a person could be exposed to harmful UV rays as a result. Hence it is preferable to configure the controller 150 to err on the side of determining occupancy. If occupancy is falsely determined, the time-out period will ensure that decontamination will take place eventually. But for any room that is used with any regularity, well before the time-out period expires someone else will likely enter the room, which will cause controller 150 to establish a condition of possible non-occupancy and shut off the lights, resulting in the new occupant actuating the lights and resetting the system to an accurate determination of occupancy. Hence, while it is preferable to include a time-out period, it is not necessary in every embodiment.

In one alternate embodiment, the controller 150 may take into account whether it is the sensor hardware that detected a condition or the light actuator that detected light actuation in determining what to do next. In one example, the controller 150 determines room occupancy in the case of light actuation, but in the case of a (e.g.) door use, the controller 150 merely re-establishes a condition of possible room non-occupancy, resetting the safety time period if one is used. Likewise, when room occupancy is detected, the controller 150 may take into account whether it was because of sensor data or light actuation and establish a possible condition of room non-occupancy differently depending on which was the cause of determining room occupancy. For example, if room occupancy was determined on the basis of a detected user light actuation, the controller 150 may not use the time-out period. In that case room occupancy is considered reliably determined when it is determined based on a light actuation detection and non-occupancy will never be established until sensor data indicates a change of occupancy.

In an alternate embodiment where the user input device is not necessarily a light actuator, user input device may provide different options for causing the controller 150 to establish a possible condition of room non-occupancy differently on the basis of the particular user input action performed. For example, the user input device may comprise several input means (e.g. buttons) for causing different time-out periods. Thus there may be a "15 minute", "30 minute", "45 minute" and "60 minute" button for requesting respective delays before reconsidering room occupancy (e.g. establishing a condition of possible room non-occupancy). In one particular embodiment, the user input device is a light actuator but is a light timer. Many users will be familiar with light timers provided in public places to ensure the lights are shut off after use of a room (e.g. hallway or staircase). The user input device may be such a light timer, based on the input to which the controller 150 will determine the time-out period. In a simple example the time-out period may be the same as the time input by a user on the light timer. But alternatively, the controller 150 may cause the visible lights source 155 to deactivate at the expiration of the time selected on the light timer and establish a condition of possible non-occupancy at another time, e.g. later. For example, the controller 150 may select the time-out period to be longer than the timer input by 15 minutes. Alternatively, the controller 150 may keep the same time-out period always, but the lights may be controlled according to user input on the light timer. This allows a saving in energy from the lights, while maintaining the safety time margin used by the controller. Since any activation of the lights will cause the controller to determine occupancy, there is no danger in deactivating the lights before the end of the time-out period.

In this example, while a user light actuation is the basis of determining room occupancy, another user light actuation, even if it turns off the lights, is not a basis for establishing a condition of possible or confirmed non-occupancy since even after turning off the light, the user may still be in the room. When a door sensor is used, even after turning off the light, the user may still be in the room so door sensor data is used to establish a condition possible of room non-occupancy.

Returning to FIG. 4, in the example shown, no door movement or light actuation is detected. Hence, at the end of the safety time period, the controller 150 establishes a condition of confirmed non-occupancy 215. This may be preceded by warnings, as described above. The controller may also cause warnings once the condition of confirmed room non-occupancy 215 is established. This can be in audio or visual forms as described previously. For example the controller 150 may cause the lit-up light actuator to start flashing boldly and cause audio instructions to leave the room immediately or to press the light actuator button to play over a speaker (not shown).

In response to establishing the condition of confirmed non-occupancy, the controller initiates a room decontamination operation. In this particular example, the decontamination hardware 115 is UV room decontamination hardware and the controller 150 initiates a decontamination operation by causing the UV lamp 120 to activate at step 445 via communication 440. To do this, the controller 150, may use any suitable means. In this example, UV lamp 120 is connected to the controller 150 by its power input and the controller 150 is configured to decide whether power is provided to the UV lamp 120. In this example the decontamination hardware interface 154, which here is a UV light source interface, may simply be a pair of terminals connected to power cables 165 of the UV lamp 120 to which the controller 150 can selectively provide power. Thus the controller 150 may communicate through the decontamination hardware interface 154 with the decontamination hardware 115 to cause it to selectively activate or deactivate simply by selectively providing it power. Of course, decontamination hardware interface 154 if configured to selectively provide power to the decontamination hardware 115, does not need to directly feed power to the UV lamp 120, it could be connected to a relay or other switching mechanism for causing the power to be selectively provided to the UV lamp 120. The same applies to the visible light source interface 151.

It is to be understood that in alternate embodiments, the controller 150 may be configured to communicate differently with the decontamination hardware 115. For example, the controller 150 may be configured to provide power in different ways to operate the decontamination hardware 115 differently. Alternatively the controller 150 may be configured to selectively provide power to different aspects of the decontamination hardware 115. For example, the controller 150 may be configured to selectively provide power to different UV lamps, or to the ventilator 170 to control operation of such different aspects of the decontamination hardware 115. Of course, control of the decontamination hardware 115 does not need to be performed by controlling input power. Decontamination hardware may be controlled in other manners using signaling. For example, digital signaling can be used to control decontamination hardware that is independently-powered and controllable by such signaling. To this end, the decontamination hardware interface 151 may be a digital interface such as a USB interface. Other embodiments are possible. For example decontamination hardware 115 may be controllable by remote-control-type infrared signals and the decontamination hardware interface 151 may comprise an IR transmitter or an output to an IR transmitter.

Returning to the example of FIG. 4, in this example the decontamination hardware 115 is UV decontamination hardware and it is controlled by the controller 150 by selectively providing power to the UV decontamination hardware. Upon establishing the condition of confirmed non-occupancy 215, controller activates the decontamination hardware 115 by causing power to be provided to the decontamination hardware 115, which causes the UV lamp 120 to turn on and the ventilation system 170 to activate. In this particular example the UV decontamination hardware interface 151 controls a relay which selectively provides power to the decontamination hardware 115.

Thus a decontamination operation is initiated. While conditions of confirmed non-occupancy 215 are established, the controller 115 monitors sensor data. The controller 150 determines, at least in part on the basis of the sensor data, whether safe conditions for decontamination exist in the room 105. In this example, safe conditions for decontamination are, as described, the non-occupancy of the room. Also as described, the controller 150 determines whether the room is non-occupied in part on the basis of the sensor data, which tells the controller 150 when the door has been used. The controller 150 also determines whether safe conditions exist based on whether a light actuation occurs. As we've seen, the absence of a light actuation is used to determine safe conditions. Similarly, depending on the conditions sensing hardware 40, safe conditions may be determined precisely when no sensor data is received. For example, if the condition sensing hardware 140 provides data input to the controller 150 only when the door is used (or a movement detector detects movement, or both, etc. . . . ) the absence of a signal from the conditions sensing hardware 140 may be what the controller 150 uses to determine safe conditions. In such a case, the controller 150 is still said to determine at least in part on the basis of sensor data whether safe conditions exist because the controller 150 uses the absence of data to this end (and conversely the presence of data or data itself are used to determine that safe conditions do not exist in the room).

The controller 150 continues to monitor sensor data throughout the decontamination operation and causes interruption of the decontamination operation if safe conditions cease to exist. In the case of UV radiation decontamination, interruption involves causing the UV decontamination hardware to stop radiating UV light. In this example, the controller 150 monitors sensor data and when the door sensor 141 detects use of the door 110, this is communicated to the controller 150 and the controller 150 immediately causes deactivation of the UV lamp 120, in this case by cutting the power provided to it. In this example, the controller 150 determines a condition of occupancy 210 when a door use is detected.

The decontamination operation may be performed in any suitable way. In this example, the decontamination operation is performed until a completion is reached. Completion of decontamination can be when a desired level of decontamination has occurred such as when substantially the whole room 105 has been decontaminated, disinfected or sterilized. The desired level of decontamination may be established on any suitable basis, such as on the basis of time spent decontaminating, or on the basis of feedback. In the present example, completion is determined when a decontamination completion time has been achieved. To this end, the controller 150 may include a counter to count out the decontamination completion time. In this example, the decontamination time is an amount of time in which it is determined that all surfaces in the room 105 that are exposed to the decontamination hardware 115 have been effectively disinfected, e.g. sterilized. The controller 150 is configured to run the decontamination operation for a set amount of time, which may be hard-set, or programmable into the controller 150 (e.g. upon installation, based on the particulars of the room 105, such as room size, geometry, content and/or purpose). Completion is determined by the controller 150 when the entire decontamination completion time has elapsed without interruptions.

Completion of decontamination may alternatively be based not just on how much decontamination is required to effectively disinfect surfaces directly exposed to the decontamination hardware 115, but on how much decontamination is required to effectively disinfect more, such as all surfaces of the room 105. In the case where UV decontamination is used, this would mean accounting for enough decontamination to ensure that UV light reflected from room surfaces towards non-directly-exposed surfaces has effectively disinfected the non-directly exposed surfaces. Decontamination of just the surfaces exposed to the decontamination hardware 115 may be sufficient for many implementations as these are often the surfaces that are most commonly touched.

In the present example, the controller 150 in this example determines whether a desired level of decontamination has occurred on the basis of the time elapsed during the decontamination operation. Any interruption while the decontamination operation is in progress is indicative that not the entire set amount of time (e.g. an amount of time sufficient for the UV light to disinfect or sterilize the room) has elapsed. Therefore simple indication that an interruption has occurred during the operation can be an indication of the time elapsed during the operation insofar as it indicates that the decontamination completion time has not elapsed. It is also possible to count the time (e.g. seconds) elapsed during the operation, e.g. using the same counter that counts out to the decontamination completion time. When the time is counted, the completion status may be not just whether or not the decontamination has occurred but how much time it occurred for or what percentage of completion was achieved.

In an alternate embodiment, the system 100 may also include a decontamination sensor system to detect decontamination activity, such as the amount of decontamination that has occurred or is occurring during decontamination operations. To this end, the controller 150 may also include and interface for communicating with the decontamination sensor system. Such a decontamination sensor system may be standalone, may be included in the decontamination hardware (in which case the decontamination sensor system interface may be one and the same with the decontamination hardware interface), or be located elsewhere, such as on the controller 150 body or on the light actuator. The decontamination sensors can be a simple UV light sensor that senses the light reflected back to it from the surfaces of the room or of objects in the room. To this end, in this example, it may be positioned so as to receive no direct light from the UV light source. It can output a Boolean output indicative of whether or not it has cumulatively detected UV light in sufficient quantities, e.g. in quantities sufficient to indicate disinfection or sterilization of the room. The UV light sensor may also not simply monitor how much UV light in total it has detected, but rather it may detect whether or not it has detected UV light in sufficient quantities for a sufficient amount of time, e.g. to achieve disinfection or sterilization. The output may be the Boolean value representative of whether it has reached a threshold of UV light detected, or it can output data indicative of the amount of UV light it has detected (altogether or over time). In such a case, completion status can be not simply whether or not the decontamination has occurred but rather it may indicate how much decontamination has occurred as a function of how much UV light was received by the UV light sensor.

In an embodiment where decontamination completion is not taken into account, the decontamination operation may continue as long as the conditions of confirmed non-occupancy remain established. In other words, the decontamination hardware 115 keeps working until safe conditions cease to exist. E.g. the controller 150 keeps the UV lamp 120 radiating until the door sensor 141 detects door use or until a light actuation occurs.

In this example, however, the decontamination operation ceases when the decontamination completion time has elapsed. Although the controller 150 is capable of initiating and interrupting decontamination operations, it is not required that the controller 150 causes the decontamination operation to stop once the decontamination operation time has elapsed. In this example the controller 150 is in charge of counting the decontamination completion time and does turn off the decontamination hardware 115 upon completion (in this case by cutting power to it) but in an alternate embodiment, the timer may be on the decontamination hardware 115 itself with the controller 150 merely sending an "initiate" and "interrupt" signals. The decontamination hardware 115 may also send feedback informing the controller 150 when decontamination is occurring (which could be used by the controller 150 for safety measures to activate alarms or warning if decontamination wrongly occurs when the controller 150 has not requested it or if decontamination continues after an "interrupt" signal has been sent; or merely to confirm that "interrupt" signals are properly received and re-send if they aren't). But even in a system without such feedback, the controller can nevertheless ascertain whether completion has been achieved on the basis of whether or not it has had to interrupt a decontamination operation before completion (e.g. by also counting the completion time).

Once a decontamination operation has completed, this may be seen as optional state 220 where a condition of confirmed non-occupancy is still established but a decontamination operation is not underway. In this state 220, the controller 150 keeps the decontamination hardware deactivated, the visible light source 155 deactivated, and continues to monitor the condition sensing hardware 140 so as to know when the occupancy changes.

Optionally, the controller 150 may count an inter-operations time after which another decontamination operation is initiated. In some settings, it may be desired to perform decontamination operations with a certain frequency. This may be to ensure that any pathogens not eliminated in the last decontamination cannot spread again, or to make sure that pathogens on surfaces or in air not reached by the last decontamination operation do not spread to surface or air that can be decontaminated. Ensuring a certain frequency of decontamination may also be useful in promoting confidence in the cleanliness or sterility of the room 105. In some instances, the time since the last decontamination may be presented to users of the room 105 or others, and it may be desirable to keep this time short in order to promote a perception of cleanliness or sterility. Moreover, time between decontamination operations may be logged and kept for the purpose of ensuring adherence to hygienic standards or otherwise to be able to show that decontamination has occurred e.g. at a certain frequency.

Whatever the reason, in this example, the controller 150 waits a certain inter-operation time after a completed decontamination operation. To this end, the controller 150 may have a timer for counting out the inter-operation time. The reader will appreciate that timing of the various time periods described herein can be done by a single timing arrangement embodying all the timers if suitably configured. If the inter-operation time elapses with no change in occupancy status, the controller 150 initiates another decontamination operation and returns to the state 215. However, if the controller 150 detects occupancy (e.g. in response to sensor data or to a detected light actuation) the controller determines room occupancy 210.

While in the above example the controller 150 counts out an inter-operation time while in state 220 upon the lapse of which it initiates another decontamination operation, it will be appreciated that the controller 150 could alternatively merely remain in state 220 until occupancy status changes. Alternatively, the controller 150 in state 220 could also determine when to initiate another decontamination operation based on factors other than time such as based on a pre-set decontamination schedule.

Controller 150 is configured to initiate a room decontamination operation when safe conditions for decontamination exist in the room, in this case when a condition of confirmed room non-occupancy is established. However, the room decontamination operation does not necessarily have to be initiated in response to safe conditions or confirmed non-occupancy. For example, the controller 150 may be configured to cause decontamination on a scheduled basis. In such a case, the controller 150 may determine that safe conditions exist (in our example that conditions of confirmed room non-occupancy are established by the controller 150) but doesn't initiate a decontamination operation until a decontamination operation is scheduled. In this case, state 215 is replaced by state 220.

When the controller 150 causes decontamination on a scheduled basis, the controller 150 may deal with occupancy during scheduled decontamination times in any suitable manner. In one embodiment, if a scheduled decontamination time occurs while a room occupancy is determined or a condition of possible non-occupancy is established, the controller 150 merely waits until a condition of confirmed room non-occupancy is established and initiates the decontamination operation then. If another scheduled decontamination time occurs before the last one is completed, the controller 150 may perform two decontamination operations as soon as possible or may simply drop the last one. In that case, the controller 150 may make a note in the historical decontamination operations log (described herein) that that scheduled decontamination did not occur.

FIG. 5 illustrates a decontamination operation interruption. Here a decontamination operation 505 is under way when the door sensor 141 detects use of the door 110. Sensor data 515 indicative of the use of the door is received by the controller 150. As has already been described, the sensor data shown here as a discrete signal could be a state of open circuit. Controller 150 monitoring the sensor data determines room occupancy on the basis of the sensor data. In response the controller 150 interrupts the decontamination operation, in this case by causing the decontamination hardware 115 to deactivate via communication 530. In this example, the decontamination hardware 115 is UV decontamination hardware and the communication 530 is a cutting of the power supplied to the decontamination hardware 115. The controller 150 also causes the activation 545 of the visible light source 155 via communication 540 (e.g. re-establishing power to the visible light source 155) if they were maintained deactivated during the decontamination operation. As will be described herein the controller 150 may also log 550 decontamination operation data after interruption.

Figure 7:
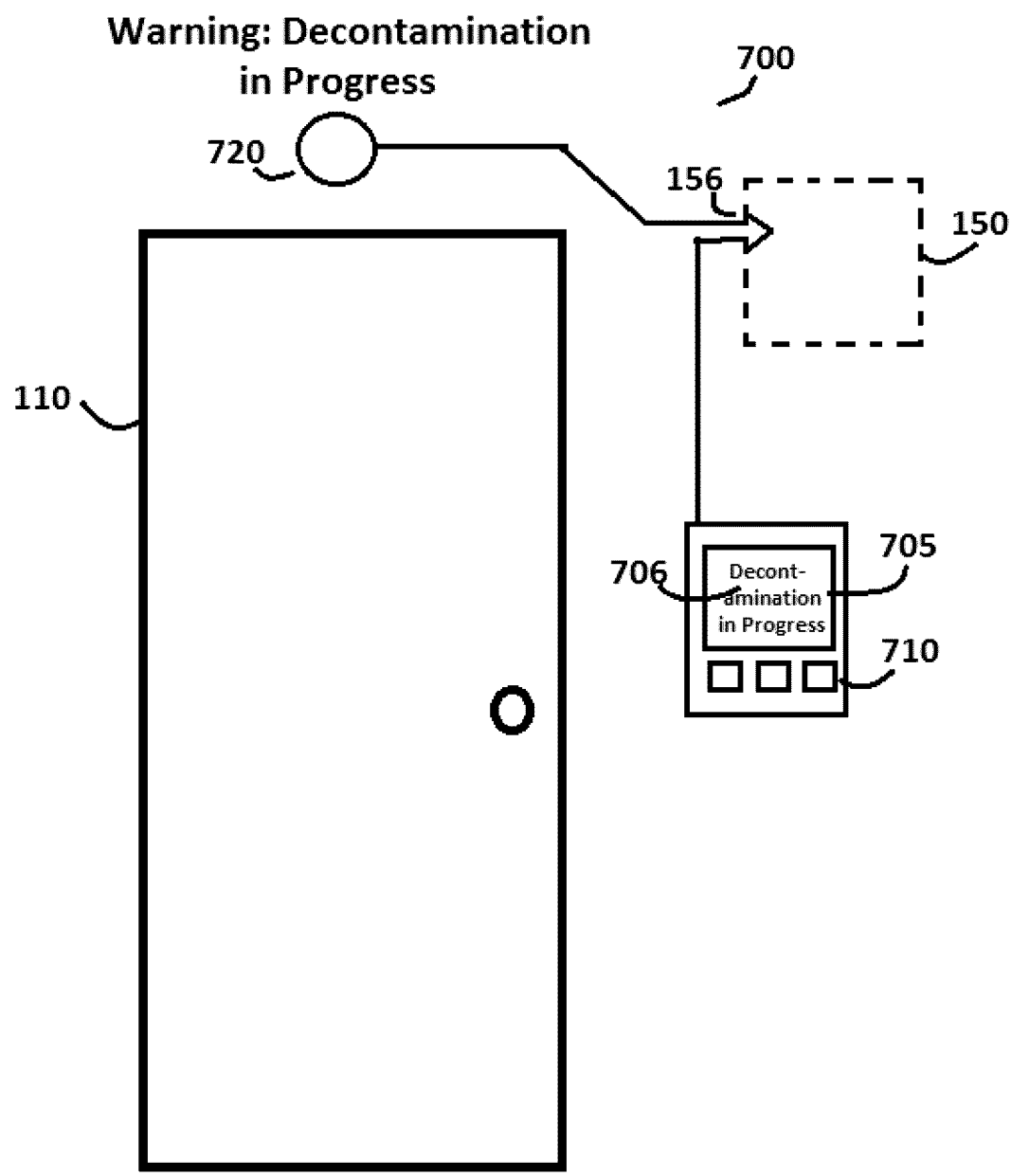
FIG. 7 is a front view of the entrance to the room shown in FIG. 1.

FIG. 7 shows external hardware 700 that may be present in system 100. In this example, the external hardware comprises an external display 705 an external input 710 and a visual warning indicator 720. The external hardware 700 is controlled by controller 150 which comprises an external hardware interface 156 for that purpose. The external hardware interface 156 is suitable for communicating with all the external hardware 700, and although it is shown here as a unitary, it will be appreciated that it can comprise different constituent parts to communicate with different pieces of hardware. Although the controller 150 is shown here as being on the other side of the wall, it will be understood that this is just an example. In fact the controller 150 may be located anywhere convenient. In one exemplary embodiment, the controller 150 is integral with the display 705.

The external hardware interface 156, may be any suitable interface means for communicating with the external hardware 700. For example, the external hardware interface 156 may include an arrangement similar to the visible light source interface 154 to control the visual warning indicatory 720. To instruct the external display 705 to display certain things, the external hardware interface 156 may include a suitable display interface such as a VGA or HDMI interface. For receiving input from the external input 710, the external hardware interface may include any suitable arrangement, which may be a serial interface.

The external display 705 is a display device suitable for providing information on decontamination operations. The controller 150 is configured to control output of the external display 705 to cause the display of information on decontamination operations. In the present example, the external display is suitable for, and controlled by the controller 150 to, display a visual warning that a decontamination operation is in progress to someone outside of the room 105 is provided. In the example shown in FIG. 5, the external display is presenting a visual indicium 706 communicating the fact that a decontamination operation is in progress. In this example, the visual indicium 706 is simply a textual message communicating that a decontamination operation is in progress, but a pictorial of video representation could also be provided. Controller 150 is configured to cause the external display 705 to present this indicium whenever a decontamination operation is in progress for example to encourage a potential occupant considering entering the room to wait until decontamination has been completed. In addition to the indicium 706, the external visual display 705 could also present instructions to potential occupants instructing or encouraging them to wait until decontamination is completed and/or instructing them as to how to interrupt the decontamination operation.

If the decontamination operation is timed, such as when completion of the decontamination operation is based on duration, the controller 150 may also cause the external display 705 to display the decontamination time remaining. In certain cases, displaying the time remaining may give potential occupants (e.g. people wanting to use the bathroom if room 105 is a bathroom) more information to decide whether the time remaining is a tolerable for them. Thus displaying the decontamination time remaining can result in a decreased number of decontamination operation interruptions.

Another optional component of the external hardware 700 is the visual warning indicator 720. The visual warning indicator 720 is suitable for providing a visual warning that a decontamination operation is in progress to someone outside of the room 105 is provided. This indicator which may be present instead of, or in addition to, the external display 705 and serves the sole purpose of indicating when a decontamination operation is in progress. The visual warning indicator 720 may simply be a signal light, preferably located near a sign indicating it's meaning, such as a sign saying "Decontamination in progress when light flashing". The visual warning indicator may be used with an external input 710 consisting of a single "cancel decontamination" button, particularly when no external display 705 is present. In such a case, the visual warning indicator 720 informs people outside of the room 105 that decontamination is in progress such that they can choose to wait completion before entering the room 105 if possible. Without any indicating means, even a user willing to wait out the decontamination operation may have no way to know that decontamination is ongoing and will therefore unwittingly interrupt a decontamination operation when ongoing by entering the room 105. Thus the visual warning indicator 720 may reduce the number of interrupted decontamination operations, leading to a better decontamination record. The visual warning indicator 720 may also serve to discourage some potential occupants from interrupting the decontamination, and to seek another room (e.g. bathroom) if available.

The external input 710 is optional and can be any hardware suitable for receiving input from a user. In one example, the external input 710 is a touchscreen collaborating with the external display 705 to receive input from users. In this example, however, the external input 710 is merely an array of buttons. The controller 150 may be configured to receive input from external input 710 indicative of a user's intention to interrupt a decontamination operation. In this manner, a potential occupant can be given another way to interrupt decontamination operation other than opening the door 110 or otherwise creating a condition not safe for decontamination. For example, while the decontamination is in progress, the external display 705 may display instructions to press a particular button in the button array to interrupt the decontamination operation. If a user presses the particular button, the external input 710 communicates this to the controller 150. The controller 150 may treat the button pressing in the same manner as a light actuation, determining room occupancy 210. In this example, however, the controller 150 distinguishes between a light actuation and an interruption caused by the external input 710 and in the case of the latter, the state 220 of confirmed non-occupancy with decontamination operation non underway is assumed.

While the external input 710 is shown as a single unit button array near the external display 705, it will be appreciated that it may be distributed. For example, a lone "cancel decontamination" button may be spaced away from the external display 705 and other buttons/elements of the external input 710 and, e.g., be labeled and caused to flash during decontamination operation in a manner similar to that described in relation to the light actuator 145 as it behaves during conditions of possible room non-occupancy.

Figure 10:
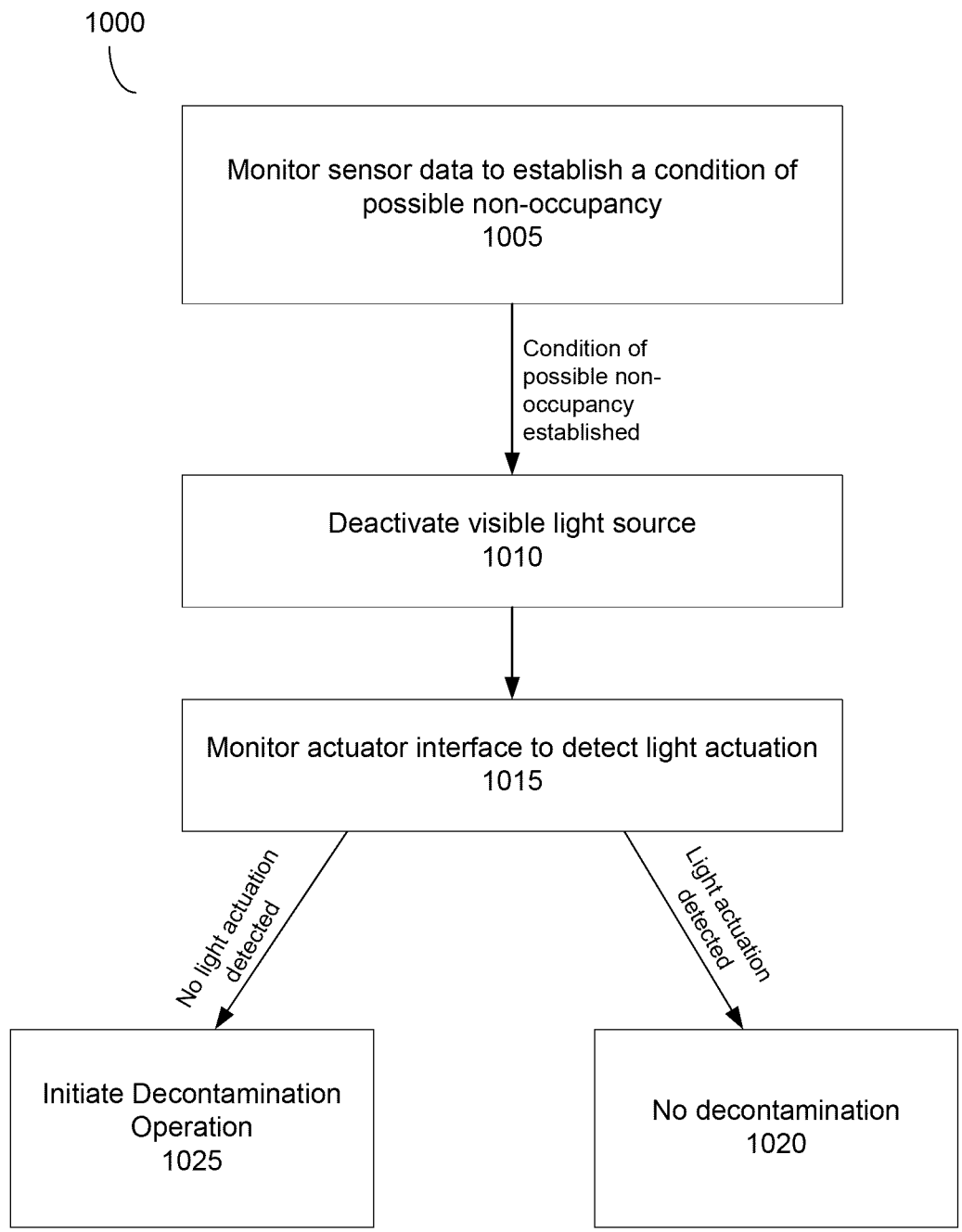
FIG. 10 is a flowchart illustrating a method for safely applying a UV decontamination operation according to a non-limiting embodiment.

FIG. 10 illustrates a method 1000 for safely applying a UV decontamination operation in room 105 in accordance with teachings provided here. The method may be undertaken by the controller 150. At step 1005 the controller 150 monitors sensor data generated by condition sensing hardware to establish a condition of possible room non-occupancy. Once the condition is established, at step 1010, the controller 150 deactivates the visible light source. The controller 150 then monitors the actuator to establishing to detect the presence of a user light actuation. If no user light actuation is detected, at step 1025 the controller establishes a condition of confirmed room non-occupancy and a room decontamination operation comprising the activation of a UV light source in the room is initiated. If a user light actuation is detected, at step 1020 the controller determines a room occupancy condition and no decontamination operation is initiated.

Figure 8:
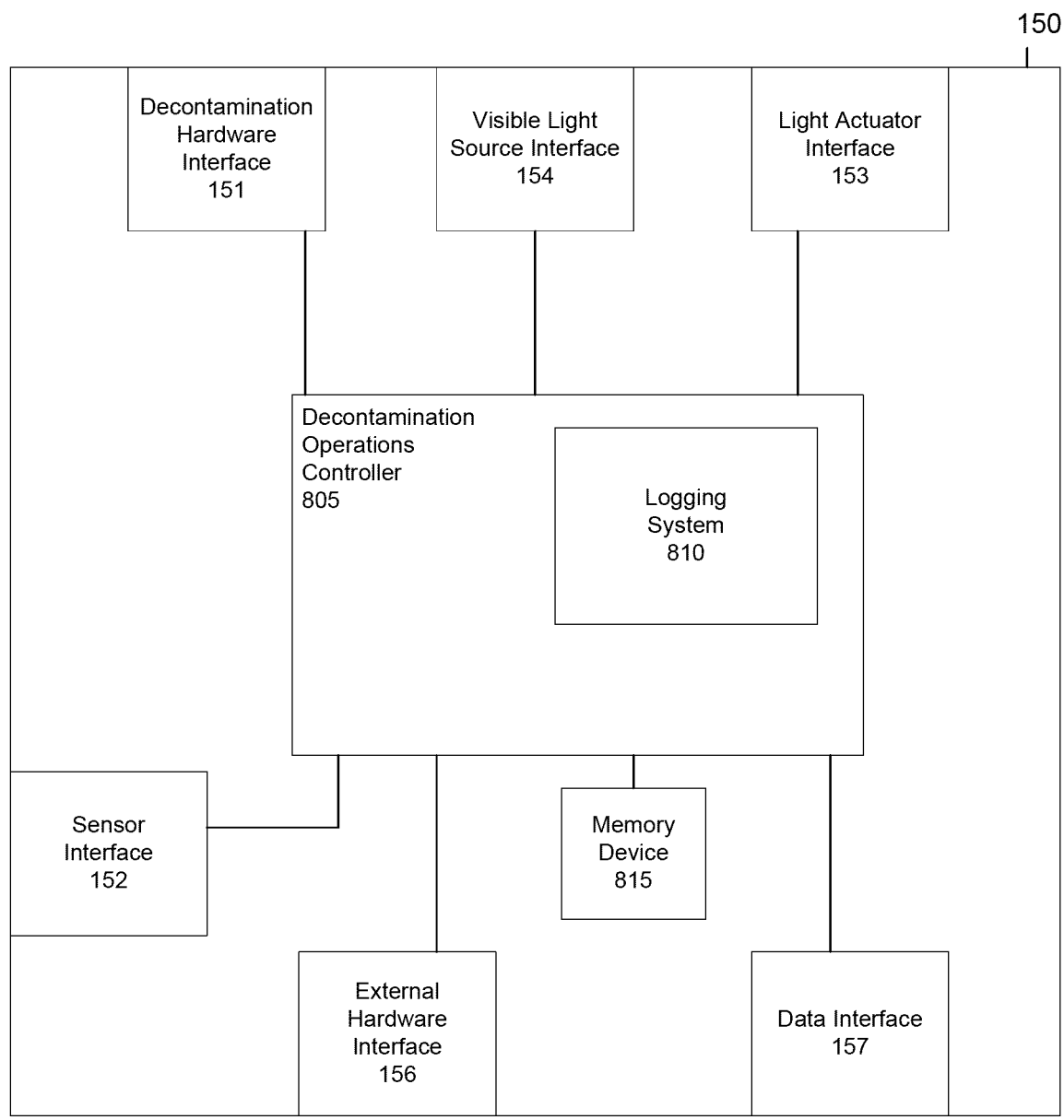
FIG. 8 is a block diagram illustrating the room decontamination system controller for the system shown in FIG. 1.

FIG. 8 shows a modular diagram of an exemplary embodiment of controller 150. In the present example, the controller 150 comprises the decontamination hardware interface 151, the visible light source interface 154, the light actuator interface 153, the sensor interface 152, and the external hardware interface 156 described above, as well as a data interface 157 and a memory device 815. Function of the controller 150 is controlled by a decontamination operations controller 805. The decontamination operations controller 805 comprises a logging system 810. It will be understood that the modules shown in FIG. 8 may be physical modules or logical ones. In an embodiment where the controller 105 comprises a software-programmable CPU with a memory comprising instructions to perform the functions of the controller 105 described herein, the logging system may be a subset of the instructions dedicated to the logging functions ascribed here to the logging system 810. Alternatively the logging system 810 may be a dedicated module, such as an FPGA or a portion of an FPGA dedicated to the logging functions. Essentially, it will be appreciated that there are many ways to embody the logging system 810 and the logging system 810 is not limited to any particular one.

In this example, the memory device 815 is a local memory. The memory device 815 is shown as being internal to the controller 150 in this example, but it will be appreciated that the memory 815 could also be external. For example the memory device 815 could be local cache within a chip comprising the decontamination operations controller 805, or it could be a DRAM or other suitable memory device located outside of the same chip but accessed by the chip. Alternatively still, the memory device 815 could be an interface for a removable storage such as an SD card or other suitable removable storage.

The logging system is configured for generating decontamination operation data representative of decontamination operations initiated by the controller 150 and for populating a historical decontamination log with the decontamination data.

Decontamination operation data is any data describing a particular decontamination operation. The decontamination operation data can be created in any suitable digital medium. For example, the decontamination operation data can be individual files created by the logging system for each decontamination operation. Alternatively the decontamination operation data can be created as database entries in a database which may embody the historical decontamination log. Alternatively still, the decontamination data may be a particular data structure created for the purpose of storing decontamination data. Likewise the historical decontamination operations log may be any suitable arrangement for storing decontamination information. For example, the historical decontamination operations log may be a data structure such as a linked list holding decontamination data entities. Alternatively the decontamination log may be a database as mentioned above. In another example, the historical decontamination operations log may be a repository of decontamination data file. In yet another example, the historical decontamination operations log is a textual file comprising textual list of entries consisting of the decontamination operation data in text form.

The logging system 810 creates decontamination operation data describing individual decontamination operations. In the present example, the decontamination operation data comprises completion data indicative of a level of completion of the decontamination operation. In the present example the completion data indicates whether or not the decontamination operation was completed, the levels of completion being either completed or not completed. Alternatively, however, the completion data may include a scale of completion. In the example where completion is determined based on a decontamination completion time, the logging system 810 may record the decontamination time as completion data such that if the decontamination operation was not completed, the completion data would indicate the amount of time that the decontamination operation ran. In another example, where a decontamination sensor system is used to ascertain decontamination completion, the completion data may be based on decontamination sensor data indicative of decontamination activity, such as an amount of UV light absorbed by a UV sensor. Whatever the method used to ascertain completion, completion data may be presented as raw data or be representative, such as a percentage or a level on another scale.

In the present example, the decontamination operation data also includes a decontamination operation time at which the decontamination operation occurred, e.g. the initiation time of the decontamination operation. To this end, the controller 150 comprises, or has access to, a timekeeping device from which it derives the time and date which it ascribes to the decontamination operation data. Optionally, the decontamination operation data may include an identifier uniquely identifying the particular decontamination operation data from among other decontamination operation data that may be found in the historical decontamination operations log. In the present example the initiation time serves as the unique identifier.

Generation of decontamination data can occur at any suitable time. In the present example, the decontamination data is written into memory as it is generated in multiple steps. In particular, when a decontamination operation is initiated, the logging system will access the historical decontamination operations log, in this case a text file, and write into it the initiation time of the decontamination operation in progress. When the decontamination operation terminates, either being completed or interrupted, the logging system then writes into the text file the completion data associated with the decontamination operation. Thus, although generating decontamination data is shown as ongoing during a decontamination operation in FIG. 4 at step 450 and FIG. 5 at step 505, it is to be understood that generating the decontamination operation data can be done at one or more discrete points in time before, during or after the decontamination operation. Likewise, although logging decontamination operation data is shown as a discrete separate step 550 in FIG. 5, it is to be understood that populating the historical decontamination operations log may happen simultaneously with the generation of decontamination operation data, as is the case when the data is created directly in the text file embodying the historical decontamination operations log.

The logging system 810 may in certain embodiments also generate other data. For example, the controller 150 receiving sensor data may also use sensor data to keep track of the uses of the room 105. In the case of a single-user bathroom, the controller 150 may interpret a door opening when the room is determined to be occupied as a user having left. When the door opens next, or if the light actuator is actuated, the controller 150 determines that a new user has entered the room. In response, the logging system 810 may increment a user counter and/or store as usage data the instance of a user having used the room. Usage data may be stored in a separate log, which may have a configuration like the ones listed above for the historical decontamination operations log. In this example, however, usage data is stored in the historical decontamination operations log. In particular it is stored as textual entries in between decontamination data. Usage data may merely indicate an instance of room use or they may include more information such as time of use and/or duration of use. Instead of entering discrete usage data for every use, the logging system 810 may bundle together several uses into one set of usage data, for example by entering as usage data the number of users that have used the room 105 since the last decontamination operation. To this end, the logging system 810 may include a counter for counting users and enter usage data into the historical decontamination operations log before decontamination data at the occasion of the next decontamination operation. In another example, however, the logging system 810 enters usage data indicating that a user has used the room when the first user after a decontamination operation enters the room, and updates the usage data in the historical decontamination operations log when additional users enter the room by modifying a counter value in the log. In the present example, the logging system stores discrete usage data for every use in the log and the usage data include time and duration of use. In this example, for the usage data also includes what state the controller considered the room to be in (e.g. whether the controller had established a condition of possible non-occupancy or a condition of confirmed non-occupancy of the room) just prior to the user entering the room.

As described, the historical decontamination operations log may include the decontamination data for past decontamination. In the present example, the logging system 810 is also configured to eliminate entries past a certain time. Decontamination data may be eliminated based on relevancy, e.g. being older than a certain threshold, or merely based on space available in the historical decontamination operations log.

The historical decontamination operations log makes it possible to know about past decontaminations. This is an extremely useful tool which allows the system owner to track the use of the system 100 and the decontamination status of the room 105 through time. Installing decontamination systems can reduce other costs by reducing the necessary frequency of bathroom cleaning by cleaning staff. Nonetheless such systems can be costly and therefore demonstrability of benefits can be an important asset to both the procurer and the provider of such systems. Operators of a facility, such as a hospital or a nursing home, may earn a promotional advantage by being able to demonstrate room decontamination activity. Moreover, having access to historical records may allow the facility operators to know when physical cleaning is necessary or at what frequency it is necessary. In an interruptible decontamination system, merely scheduling decontaminations or setting decontaminations to occur when possible does not necessarily guaranty that they will occur with any particular regularity. Having access to a historical decontamination operations log allows the operator to not only know and verify whether decontamination operations happen with a desired frequency, but also to demonstrate it to concerned individuals such as patients/clients and/or regulatory agencies. In addition, a historical decontamination operations log can also expose problems with the system 100 or its use. For example, if the door 110 is kept constantly open, this will result in no decontaminations occurring. Whereas in the absence of a log this may go unnoticed, with the log an administrator can identify that there is a problem with the room 105 or system 100 and fix it, such as by installing a door closer. For these and other reasons, access to the historical decontamination operations log is a tool that can drastically increase the usefulness and effectiveness of a room decontamination system.

In certain cases, having access to decontamination records can be of critical usefulness in proving due diligence in maintaining good hygienic conditions. For example, if a hospital patient contracts an infection following a hospital visit, and decides to sue the hospital for having unsanitary conditions, the historical decontamination operations log may provide vital proof to show that, e.g., the particular patient's bathroom was indeed sterilized at the time that it was used by the patient. Here the example of a hospital setting and bathroom was used, but it will be appreciated that in other types of facilities and for other room, having records showing decontamination history can serve as important evidence of responsibility (or more importantly, lack thereof) in the propagation of one or more infections.

Depending on the requirements of the system 100 or on intended use, the historical decontamination operations log may include decontamination data for any past decontamination or for only those decontamination that have been completed. In one example wherein the log is used to ascertain whether the room 105, only decontamination operations that have been completed are kept in the log because partial decontamination operations are not considered useful information. However, decontamination data on partial decontamination operations can also be useful to an operator to know how often decontamination operations are interrupted. In the present example, the logging system 810 includes decontamination data on incomplete and complete decontamination operation in the log. The data on incomplete decontaminations and usage data helps paint a better picture of the use of the system 100 and can be used by an operator to identify issues. Optionally, the operator may be able to fine tune the controller 150, e.g. by interfacing with the external input 710, to vary thresholds such as time-out period, safety time period and inter-operation time to prevent common situations that prevent completion of decontamination operations. In other embodiments, the decontamination completion time can also be modified, although in this example, the decontamination completion time cannot be changed by an operator after system installation because it is set based on requirements to achieve effective decontamination. Optionally, the controller 150 may be configured to analyse the historical decontamination information itself, and to modify the threshold according to use. For example if the controller finds a high ration of time-out occurrences to users entering the room during a condition of possible non-occupancy, the controller 150 may reduce the time-out period incrementally until the ratio hits a predetermined threshold. As such the controller 150 may be a self-regulating controller.

The historical decontamination operations log may be used to ascertain whether the room 105 meets a certain hygienic standard. The hygienic standard may be any particular standard, such as an operator-set quality assurance standard, a desired hygiene objective for the room, an industry standard or a regulation. Some industries may be subject to regulations requiring decontamination, disinfection or sterilization of certain rooms at a certain frequency, after a certain number of uses.

Hygienic standards may specify these or any other suitable constrains such as a maximum acceptable delay between decontamination. In some embodiments, the information in the historical decontamination operations log may be compared to a hygienic standard to determine whether the room meets the hygienic standard. This may be done by the controller 150 or by a remote device receiving the decontamination operation data or the historical decontamination operations log, or parts thereof, from the controller 150 as described herein.

In this example, the historical decontamination operations log is stored by memory device 815. The controller 150 is configured to cause the output of at least a portion of the decontamination operations log. In this example, the controller is configured for outputting past decontamination information onto external display 705.

As has been described herein, when a decontamination operation is in progress, the controller 150 causes the external display 705 to display an indication of this. When no decontamination operation is in progress, the controller 150 may cause the external display 705 to display a visual representation of historical decontamination data. In this example, the controller 150 causes to the external display 705 to indicate the amount of time that has passed since the last completed (successful) decontamination operation. To this end, the controller 150 may access the historical decontamination operations log in memory device 815 to identify from the decontamination operation data for the last decontamination operation the time of the last complete decontamination operation. The decontamination operation data may include the time of completion of the decontamination operation or the time of completion may be computed by the controller 150 from the time of initiation and the duration of the decontamination operation (which may be indicated in the decontamination data, or simply known as a constant for completed decontamination operations). Using this information obtained, or deduced, from the historical decontamination operations log, the controller 150 then computes the time that has elapsed since the last completed decontamination operation and causes it to be displayed, e.g. in real-time, on the external display 710.

Figure 9A:
FIG. 9A is a front view of external hardware shown in FIG. 7 according to a particular example of use.

An example of this is shown in FIG. 9A, which shows the external display 705 displaying the time since the last completed decontamination operation and the external input 710 which in this example consists of three buttons 711, 712 and 713. As shown, the external display 705 also displays button operation information 930 indicating the function of each button. In this example button 711 is for accessing the historical decontamination operations log. Button 712 is to access settings. And button 713 is to start a decontamination operation manually, if the controller 150 determines that safe conditions for the decontamination operation exist in the room. If they do, the controller will interpret an input representative of button 713 being pressed while it is labelled "start" as an instruction to initiate a decontamination operation and will do so as described in relation to state 215 of FIG. 2.

Providing the time since the last decontamination operation allows users of the room 105 not only to benefit from the sanitizing effect of the system 100, but also to gain appreciation for its effectiveness, which may increase their overall satisfaction for the room 105, and the facilities in which it is (e.g. hospital). Moreover, this function makes it possible for facilities operators or staff to quickly see whether the room is acceptably sanitized, or more specifically whether the amount of time since the last decontamination operation is acceptable, and to ascertain therefrom whether additional sanitization is required, e.g. by manual cleaning.

In addition to displaying the time since the last completed decontamination operation, the controller 150 is also configured for causing the output of decontamination data from the historical decontamination operations log to the external display 705. In particular, the external display 705 and external input 710 together embody a user interface through which a user can interact with controller 150.

Figure 9B:
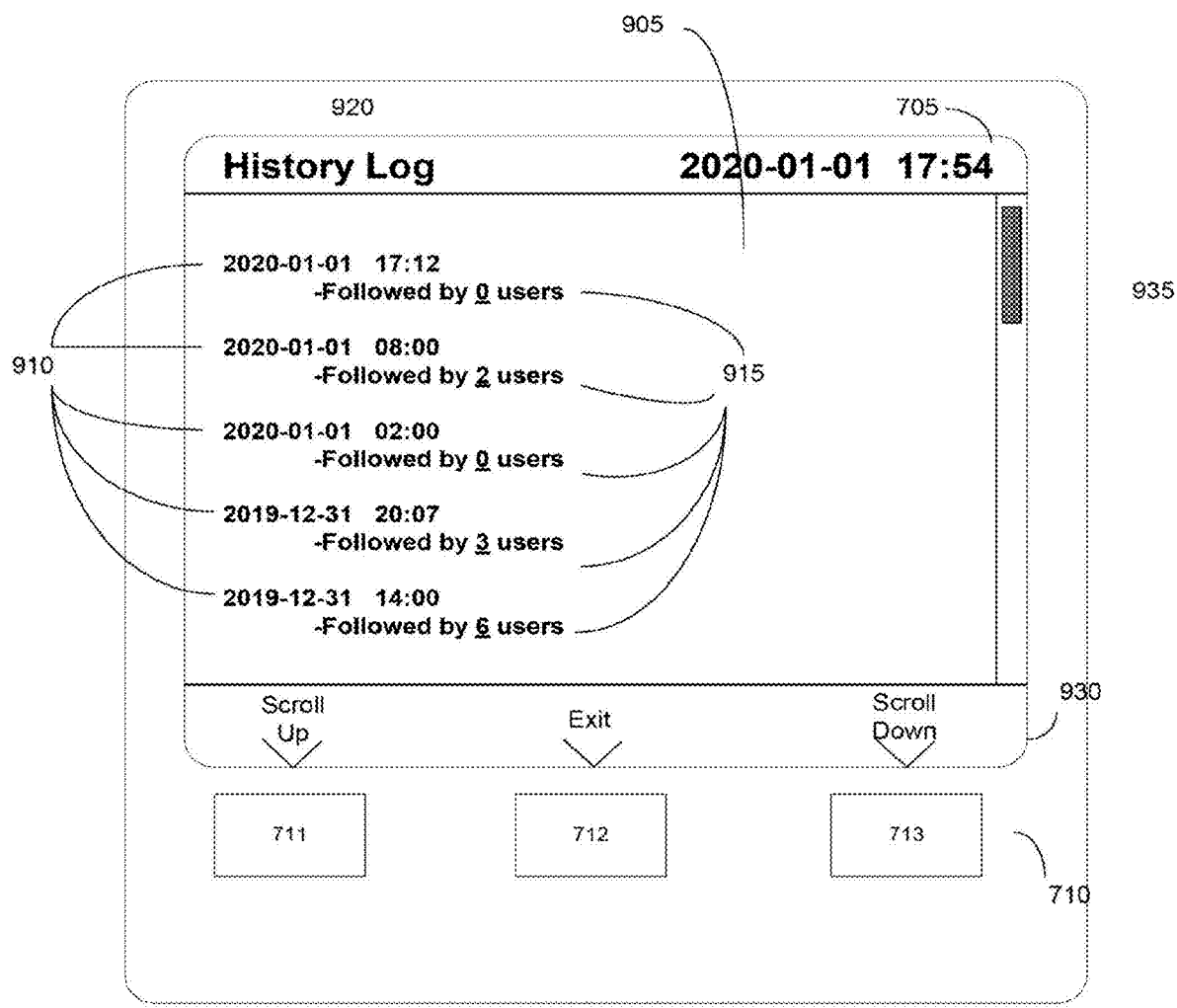
FIG. 9B is a front view of external hardware shown in FIG. 7 according to another particular example of use.

FIG. 9B illustrates the result of pressing button 711 in the example of FIG. 9A. In this case, the controller 150 causes the external display to display a visual representation of historical decontamination data and in particular a list 905 of visual representation of at least some of the decontamination data corresponding to past decontamination information. In this case, the list 905 comprises time and date entries 910 of past completed decontamination operations. As mentioned the historical decontamination operations log may contain more information than what is displayed here. As a design choice, more or less information could be displayed, for example the list 905 could include incomplete decontamination operation data, decontamination completion levels, etc. . . . . In this case the list 905 also includes, under each time and date entry 910, an indicator of how many users have occupied the room 105 after each decontamination operation. For ease of navigation, a scroll indicator 935 is also provided. Scrolling is performed using the external input 710. In this case button operation information 930 indicates that button 711 is used for scrolling down, button 713 is used for scrolling up and button 712 is used for exiting the history log. Also for ease of use, a title section 920 is provided that indicates that the history log is being displayed and provides the current time and date for reference. Optionally, additional functions can be provided, such as to select a particular decontamination operation to view additional decontamination operation data related thereto.

The reader will appreciate that this embodiment of user interface and external output/external input arrangement is purely exemplary and other compositions could be used.

Any portion of the historical decontamination operations log could be so outputted to the external display 705, the particular portion shown here being purely exemplary.

Besides outputting to a display, the controller 150 may also output the historical decontamination operations log or individual decontamination operation data to a remote device over the data interface 157. The remote device can be, for example, a computer or another computing device such as a smartphone or tablet and the data interface 157 is an interface suitable for communications with a remote device.

The data interface may include a wired interface suitable for a wire connection to connect the controller 150 to a remote device, e.g. a computer or a smartphone for uploading thereto data from the controller 150 or for receiving configuration instructions from the remote device. For example, the wired interface may be a USB interface or a proprietary interface for connecting to configuration equipment in the form of a remote device.

In the present example, the data interface 157 includes a Bluetooth™ interface for connecting to a Bluetooth™-enabled device such as a smartphone. The Bluetooth™ interface may be a data connection suitable for connecting with Bluetooth™ hardware but preferably, the Bluetooth™ interface includes all the necessary hardware including a suitable radio system and antenna for Bluetooth™-based communication. The controller 150 comprises the necessary logic for causing a Bluetooth™ file transfer. The controller 150 is configured for transferring the historical decontamination operations log, or a portion thereof, or individual decontamination operation data to the remote device. In the present example, the controller 150 can be paired to the remote device and transfer the text file embodying the historical decontamination operations log to the remote device. In this example, the text file may be viewed directly on the remote device, or transferred therefrom for viewing on another device. This is also possible when the historical decontamination operations log is in the form of any file or database in a format used by mainstream programs, or of a repository of files that are themselves readable by mainstream programs. However, if a customized data structure is used to store the decontamination operation data and/or historical decontamination operations log, the remote device may be provided with a program or app to decipher the data/log and presented in a user-friendly manner. Alternatively, the controller 150 may convert the decontamination operation data and/or historical decontamination operations log to a format suitable for use at the remote device prior to or during transfer. Even if the decontamination operation data and/or historical decontamination operations log is in a format suitable for mainstream programs, a dedicated program or app may still be used for viewing the data/log for ease of use. This may be particularly useful where communications between the controller 150 and the remote device is bidirectional, for example if the remote device may be used to configure the remote controller 150.

In the present example, the data interface 157 also includes a network interface for communicating over a network. An interface for a wired connection may be provided but in this example, the network interface is a Wi-Fi™ interface. The Wi-Fi™ interface may be a data connection suitable for connecting with Wi-Fi™ hardware but preferably, the Wi-Fi™ interface includes all the necessary hardware including a suitable radio system and antenna for Wi-Fi™ communication. Similarly to with Bluetooth™ the controller 150 is configured for transferring the historical decontamination operations log, or a portion thereof, or individual decontamination operation data to the remote device. As above, the controller 150 may be configured for transferring the text file embodying the historical decontamination operations log to the remote device. In this example, the text file may be viewed directly on the remote device, or transferred therefrom for viewing on another device. This is also possible when the historical decontamination operations log is in the form of any file or database in a format used by mainstream programs, or of a repository of files that are themselves readable by mainstream programs. However, if a customized data structure is used to store the decontamination operation data and/or historical decontamination operations log, the remote device may be provided with a program or app to decipher the data/log and presented in a user-friendly manner. Alternatively, the controller 150 may convert the decontamination operation data and/or historical decontamination operations log to a format suitable for use at the remote device prior to or during transfer. Even if the decontamination operation data and/or historical decontamination operations log is in a format suitable for mainstream programs, a dedicated program or app may still be used for viewing the data/log for ease of use. This may be particularly useful where communications between the controller 150 and the remote device is bidirectional, for example if the remote device may be used to configure the remote controller 150.

The data interface, however, may also be used for ongoing communication with the remote device, rather than a discrete file transfer. For example, the controller 150 may be partially controlled by the remote device over the network interface. In the present example, the controller 150 is configured to receive over the data interface instructions to provide certain data to the remote device. The certain data may be decontamination operation data, decontamination operations log.

The historical decontamination operations data is transmitted as a report. It can be provided in any suitable form, not necessarily as a list or in a manner reflective of the way it was collected or stored in memory. For example, the report can represent information in the historical decontamination operations data in a digested way, showing for example, the number of decontamination operations taken over one or more time periods, a frequency of decontamination operations (e.g. a minimum, maximum and/or average frequency), time between decontamination operations (e.g. minimum, maximum and/or average times), usage data, summary of alerts etc. . . . . In this example, the report comprises a standard-adherence list indicative of all the instances when the room 105 adhered to and didn't adhere to a certain hygienic standard. The controller 150 may be configured to generate reports periodically, e.g. daily, or upon request from a remote device over the data interface, or by an appropriate input by a user using external input 710. In the present example, the controller 150 is preconfigured to generate reports daily and to transmit them over the data interface and more specifically over the network to a remote computer.

The remote computer runs a computer program for communicating with the controller 150 and for receiving, storing and presenting to a user the reports. In this example, the computer program is configured to transmit instructions to the controller 150 that the controller 150 is configured to understand as instructions to perform certain tasks. In so doing, the controller 150 can be configured remotely from the remote device.

In one example, the computer program can send instructions to configure transmission of reports by the controller. In particular, in this example, the instructions may instruct the controller 150 to set a particular frequency of report transmission. The content of the reports can also be set in this manner. The controller 150 receives these instructions and in response modifies internal settings, in this example by setting internal variables that determine the frequency and/or contents of the reports. In this example the instructions to the controller can also be indicative of thresholds to set. Upon receiving such instructions, the controller 150, sets the concerned threshold (e.g. time-out period, safety time period or inter-operation time) to the indicated level, e.g. by setting variables that determine these thresholds.

In this example, the controller 150 is also configured to transmit alerts indicative of an alert condition. The alert is a form of report that indicates that a condition that requires particular attention or that is of particular interest has occurred. Alerts may not contain the same data as usually provided in reports, although such data can be included as well. They are sent on an ad-hoc basis: they are not in response to a request from the remote device nor sent on a scheduled basis. Instead, alerts are sent in response to the occurrence of an alert condition. Alert conditions can be any desired condition, and can be variably set, e.g. by instructions from the remote device. In the present example, the controller 150 is pre-configured with several alert conditions.

According to one pre-set alert condition, if the time since the last decontamination operation exceeds one day, an alert condition is raised and an alert report is sent to the remote device.

According to another pre-set alert condition, if sensor data indicates that the door 110 has not been closed for more than six hours, an alert condition is raised and an alert report is sent to the remote device.

According to another pre-set alert condition, if the controller 150 has repeatedly established a condition of possible-non occupancy only to detect a light actuation more than six times, an alert condition is raised and an alert report is sent to the remote device.

According to another pre-set alert condition, if the time-out delay elapses while the controller has determined room occupancy, an alert condition is raised and an alert report is sent to the remote device. Advantageously, this and other alerts may not only help ensure the safe and effective operation of the system 100, but may also be used as a safety device (in this example a patient safety device) to detect alarming patient conditions. In particular, if the time-out delay elapses, this is indicative of an occupant having been in the room 105 (in this example a single-user bathroom) for a very long time. This could be a sign that the occupant has lost consciousness or is paralyzed. As such, not only will the alert allow staff to verify in person that no one is in the room before a decontamination operation occurs, but it will also give them a chance to discover the patient in distressed there is a patient that lost consciousness in the bathroom. Should the door be locked, the staff will be able to prevent the decontamination operation from the outside, thanks to the external hardware 700.

According to another pre-set alert condition, if the historical decontamination operation data deviates from a hygienic standard, an alert condition is raised and an alert report is sent to the remote device. This will allow staff to come manually clean the bathroom if need be in order to guarantee the adherence to the hygienic standard. As such, the present system allows a facility operator to guarantee adherence to hygienic standard while cutting down on the labour used to clean bathroom.

Other alert conditions may be set, either as pre-set alert conditions or in response to instructions from the remote device. The controller stores data indicative of the alert conditions, and regularly consults data it has access to, such as the historical decontamination operations log or the decontamination data therein or being created and contrasts it to alert conditions to determine whether an alert report should be sent out.

Instructions from the remote device may also be indicative of a decontamination interruption. Upon receipt of such instructions, the controller 150 immediately interrupts decontamination in progress, if any.

Instructions from the remote device may also be indicative of a shutdown instruction. In response to the receipt of such instruction, the controller 150 shuts down operation and ceases to perform decontamination. Indeed, the controller 150 is also configured to shut down the room decontamination system 100. The command can be received from a remote device as mentioned, but may also be provided by other means, such as over a master switch on or connected to the controller 150 itself or over the external input 710. In the case of the latter, the shutdown command is preferably entered using a secret code such as a secret sequent of button presses so as to prevent non-staff from shutting down the system 100 at will. In this example, when the controller 150 shuts down the system 100, the controller sets the light actuator 145 to directly actuate the visible light source 155 without other consequences. This can be done in any suitable manner, but in this example a relay is provided that keeps the light actuator 145 electrically isolated from the visible light source 155, but when the relay input is unpowered, such as when controller 150 shuts down, the light actuator 145 is connected to the visible light source in such manner as to control its actuation. Alternatively, the controller 150 can simply keep the visible light source 155 on at all times while the system 100 is shut down.

Instructions from the remote device may also be indicative of a decontaminate instruction. In response to the receipt of such instruction, the controller 150 initiates a decontamination operation if safe conditions for a decontamination operation exist in the room. If they do not, the controller 150 initiates a decontamination operation as soon as safe conditions exist.

Figure 11:
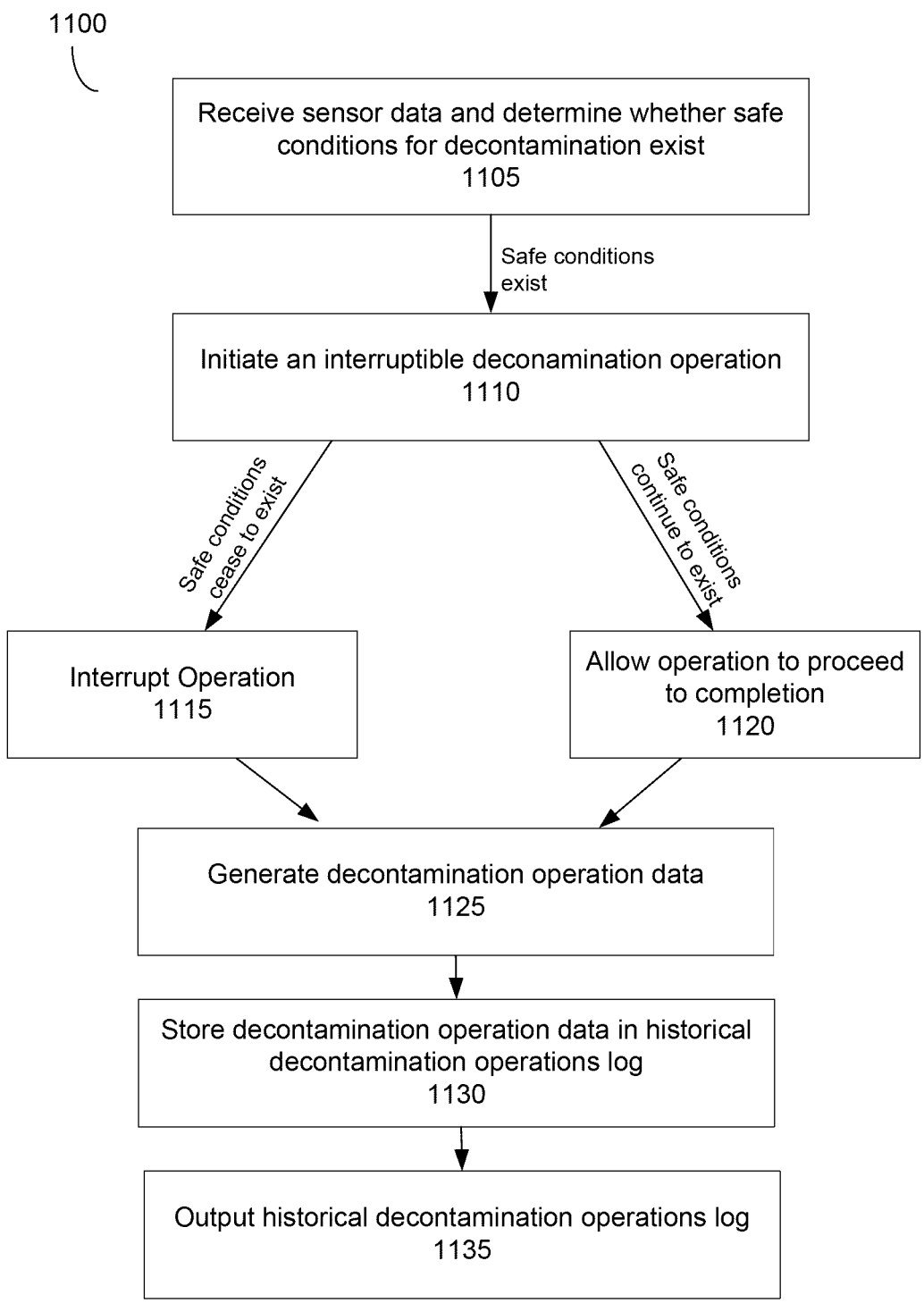
FIG. 11 is a flowchart illustrating a method for applying an interruptible decontamination operation in accordance with a non-limiting embodiment.

FIG. 11 illustrates a method 1100 for applying an interruptible decontamination operation in room 105 in accordance with teachings provided here. The method may be undertaken by the controller 150. At step 1105 the controller 150 receives sensor data from condition sensing hardware and determines, on the basis of the sensor data whether safe conditions for decontamination exist in the room. If safe conditions for decontamination exist in the room, at step 1110 the controller 150 causes the initiation by decontamination hardware of an interruptible decontamination operation on the room. If during the decontamination operation safe conditions cease to exist, at step 1115 the controller 150 causes interruption of the decontamination operation. If safe conditions continue to exist, the controller 150 allows the decontamination operation to proceed to completion as represented by step 1120. At step 1125, the controller 150 generates decontamination operation data representative of decontamination operation. At step 1130 the controller 150 stores the decontamination operation data in a historical decontamination operations log comprising decontamination operation data corresponding to more than one instance of decontamination operation. Finally, at step 1135, the controller outputs the historical decontamination operations log. Outputting can be done in any suitable manner such as in the manners described herein. As will be understood from the present description, some of the steps of this method need not necessarily occur in the order shown or may occur simultaneously.

In the present example, the sensing hardware 140 consisted only of door sensor 141. In other embodiments, other sensors could be used in addition to, or instead of, door sensor 141. To this end, the sensor interface 152 may be adapted for receiving sensor data from different types of sensors including plural different types of sensor if more than one type of sensor is used. For example, motion sensor may be used for detecting motion in the room. Motion sensors are preferably used with door sensors to detect unsafe conditions for decontamination in the room, particularly when UV decontamination is used. This is to make sure that the interruption of decontamination operations occurs as soon as the door is opened, rather than when the motion sensors detect movement, which may be after there is an opening in the door, and so prevent any leakage of UV radiation outside of the room 105 and in particular to prevent explosion the eyes of the person opening the door to UV radiation. In such a system, sensor data from the motion detector(s) may be used by the controller 150 to increase the reliability of the establishment of conditions of possible room non-occupancy and of the determination of room occupancy. In particular, the controller 150 may take into account whether motion was detected before and after door uses were detected in order to make better guesses as to the occupancy. If motion is detected after a door use, the controller 150 is configured to determine room occupancy. But if motion was sensed before but not after door use is detected, the controller is configured to determine room non-occupancy. If no motion was detected before and after door use, the controller may be configured to consider that a door opened with no one entering and establish a condition of possible room non-occupancy, or it may be configured to conclude that the motion detector is unreliable and apply the occupancy determination rules used when no motion detector is present. The controller 150 may use sensor data from a motion sensor alone, for example if no door sensor is provided. In such a case the controller 150 establishes a condition of possible room non-occupancy by determining on the basis of sensor data that no motion was detected within the room for a certain period of time. The certain period of time may be a threshold that can be modified upon instructions from a remote device as described herein or it may be hard-set. In one particular example, the certain period of time is 30 minutes.

Similarly, in another alternate embodiment infrared heat detectors suitable for detecting the heat emitted by a human body can be used in the sensor hardware 140. For the same reasons as with the motion detector, these are preferably used in conjunction with a door sensor. The infrared heat detector's sensor data may also be used by the controller 150 to increase reliability of occupancy determination, in a manner similar to that described in relation to the motion sensor. An exemplary embodiment will be described in more detail herein. Other sensors and combinations of sensors may be used as suitable for the context of the room 105.

In the example provided above, determination of decontamination completion was based on a continuous decontamination operation. In an alternate embodiment, decontamination completion could be determined on the basis of cumulative decontamination. For example, the controller 150 could determine that decontamination has been completed when a certain amount of decontamination has occurred even if there was an interruption during the decontamination operation. For example if decontamination time is the determining factor, the controller 150 may determine that decontamination has successfully occurred if cumulatively a certain decontamination time threshold has occurred even if there were interruptions in the process. Additional constraints can be used, for example an interval. In that case, the controller may determine a decontamination completion if a certain amount of decontamination time has occurred in a given threshold, e.g. 2 hours. In yet another embodiment, the controller 150 may account for germ spread in the time between decontamination, requiring an ever-increasing amount of decontamination as more time is spent during interruptions. To this end, the controller 150 may use a counter in a completion determination function to constantly vary the amount of time needed to decontaminate the room. An upper bound to the function may be used so that it goes no higher than the total time required for a complete continuous decontamination.

In the above examples, the door 110 was a hinged door and the doo sensor was adapted to detect door use for such a door. In alternate embodiment, other methods of detecting door use may be used. For example, a motion sensor on the outside of the door may detect an approach to the door before the door is even opened. This advantageously allows an extra margin of time to interrupt decontamination operations, although it may also lead to false-positive detections of door use.

Decontamination can be defined according to different thresholds. In the present example the goal of the decontamination undertaken by the system 100 was to eliminate or neutralize pathogens to a degree sufficient to effectively eliminate or efficiently reduce probability of infection. However, decontamination may be performed to other standards. In one example, decontamination may be used to disinfect the room 105 of a particular pathogen or pathogen type. For example, decontamination may be performed to the standard of eliminating or neutralizing all viruses. In another example, decontamination may be performed to achieve complete sterilization of the room 105, where substantially all microorganisms are destroyed or neutralized.

In the above example, the controller 150's interfaces were depicted as separate sub-entities. It is to be understood that this was to facilitate understanding and more efficiently convey the invention. However, the functionality of different interfaces may be combined in a single sub-entity. For example, a same USB interface may be used to connect to different hardware such as the UV hardware 115 and the light actuator 145. In such a case, the controller 150 is still considered to have a UV hardware interface 151 and a light actuator interface 153 since the USB interface is capable of embodying both those interfaces.

In another example, one or more of the decontamination hardware 115, the visible light source 155, the sensing hardware 140, the user input device 145, and the external hardware 700, or any portion thereof, may be connected to the control 150 via Bluetooth™. In such a case, the respective interfaces of the Bluetooth™-connected devices in the controller 150 are embodied by a Bluetooth™ interface in the device. Advantageously, using Bluetooth™ allows for simple installation. For example, the sensor 140 may be battery powered. Some sensors, including door sensor, can use very little battery power, allowing seamless, wireless installation of the sensor. The battery may be changed less frequently than scheduled staff cleanups, and could therefore be changed at that occasion.

In the above example, the controller 150 was shown as physically separated separate from the other hardware. This was for the purpose of better illustrating the invention. However, it is to be understood that the controller 150 is not so limited. For example, it may be beneficial for the purposes of simplifying installation to provide the controller 150 in the same container as the light actuator 145, or within the decontamination hardware 115. In such a case the controller is still has a light actuator interface 153 or a decontamination hardware interface 151 since the controller is still provided in communication with the light actuator 145 or the UV decontamination hardware 115. The fact that the controller 150 may be physically proximal to, and even provided within the same case as, another piece of hardware should not be understood to mean it does not exist.

One skilled in the relevant art will readily appreciate that the controller 150 may be embodied by suitable semiconductor-based design that can be configured to behave as described above by a person skilled in the art. Embedded systems technology may be used to embody the controller 150, as a person skilled in the art would readily appreciate upon a reading of the present description. For example, the controller 150 can be powered by a field-programmable logic array (FPGA), which can be programmed by a skilled person to configure it as described herein. Alternatively, the controller 150 can be powered by a software-programmable CPU, which is programmed by a skilled person to configure the controller as described herein. In both cases, the FPGA or CPU may interact with external components such as an external chip memory.

While in the example provided above, the controller 150 was shown to be embodied by a single unit, it will be appreciated that the controller 150 can be distributed. Different inter-operating parts of the controller 150 can be located in different physical locations. For example, the controller 150 could be constructed using different parts for performing different functions. Relays may be used in interfaces to activate or deactivate hardware, counter chips may be used to perform the functions of the timers described herein, dedicated logic gates or chips may be used to cause the controller 150 to perform the various functions it performs in the states described in FIG. 2, these things may all be provided as in separate circuitry equipment and functionally interconnected by appropriate wiring. In such an embodiment, relays may be located at or near the hardware they control, timers may be located elsewhere and so may the various logic gates or chips. In this embodiment, although the controller 150 may be deliberately distributed physically, this is not to be construed as an absence of controller 150, which is still present in the system 100 and configured to perform as taught herein.

In one embodiment, the system 100 may be retrofitable to an existing lighting system. Advantageously, this allows a room to be easily and cheaply modified to feature the system 100. In particular, a combined UV decontamination hardware 115 and visible light source 155 may be installed where the room's visible light source previously was. The circuitry already provided for the visible light source may be exploited to avoid having to rewire the entire room. As such, the UV decontamination hardware and the visible light may use the same power source, in this example the power source originally provided for the visible light source. Preferably, the previous light switch is replaced with the light actuator 145 described herein, such that it may perform as described and light up when the visible lights 155 are deactivated. The controller 150 may be provided as embedded or encased within the light actuator 145 or within the combined UV decontamination hardware 115/visible light source 155. If external hardware 700 is provided, it may be connected to the controller 150 via a wireless link, so as to avoid having to run a wire through the wall to it; the external hardware merely needs to be connected to a power source, such as a plug-in electrical outlet. In such an embodiment, the external hardware interface 156 includes a wireless interface arrangement. If a data interface 157 is provided, it may be a wireless data interface such as a Wi-Fi™ interface, or alternatively it may be provided through the external hardware 700. The sensor hardware 140, if suitable may be wirelessly linked to the controller 150. However, in the case of the magnetic contact switch described above, only a very thin wire is necessary to connect it to the controller 150, and such a wire can be run outside the wall with minimal visual impact. Advantageously, such sensors are relatively tamper-safe as disconnecting or cutting the exposed wire would cause the controller 150 to assume the door is open and that safe conditions for decontamination do not exist within the room 105. Also advantageously, should such tampering occur, the controller described above would soon transmit an alert which would allow an operator to detect the tampering. In this example, if the UV decontamination hardware 115 and visible light source 155 are combined, they may still be connected separately to the controller 150. However, if they are independently powered and controlled by the controller 150 through instructions sent by the controller, they may be connected through a combined connection and combined interface. It is to be understood that the controller is still considered to have a decontamination hardware interface 151 and a visible light source interface 154 since the combined interface is both these things.

For the purposes this description, the description of decontamination has often been simplified to surface decontamination. While surface decontamination can be an objective of the room decontamination system 100, it is to be understood that decontamination hardware and particularly UV decontamination hardware can be used to decontaminate a room of airborne pathogens as well. This was mentioned when discussing the ventilation system 170. However, it is to be understood that other aspects related to decontamination such as determination of decontamination completion thresholds and decontamination completion sensing may also be related to air decontamination. For example where decontamination completion time may have been computed to achieve surface decontamination, it may also be computed to achieve air decontamination. Where a decontamination sensor data is interpreted to determine surface decontamination it may also be interpreted to determine air decontamination. To this end, decontamination sensor hardware may also include airflow sensing hardware to ascertain whether sufficient airflow has occurred to expose substantially all the air in the room 150 to sufficient decontamination. Moreover, when discussing decontamination of surfaces in the room 105, it should be understood that this does not merely refer to the surfaces of the room itself, i.e. the walls, ceiling and floor, but also applies to other exposed surfaces of furniture and other objects in the room including fomites.

Figure 12:
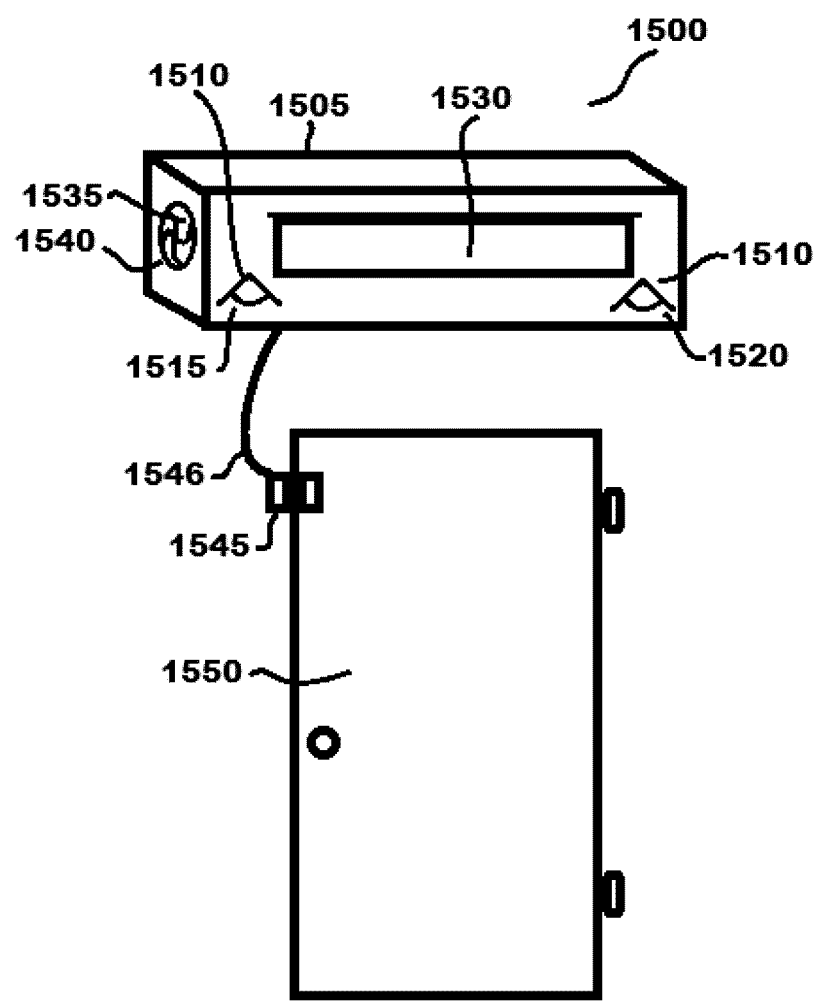
FIG. 12 shows a room UV decontamination system according to another exemplary embodiment.

FIG. 12 shows a room UV decontamination system according to another embodiment. In this example, presence detection hardware is used alongside door sensing hardware to reliably detect safe conditions for a decontamination operation. In particular, a room UV decontamination system 1500 is provided that has a body 1505 that can be installed in a room to provide UV decontamination of the room. In this example, the body 1505 is substantially unitary, comprising the majority of the components of the system 1500 (except the door sensor 1545) in a single unit, however it will be appreciated that the body 1505 could be configured differently and more distributed configurations, where different components are provided in different physical locations and suitably connected, as in the example of FIG. 1, are possible.

The body 1505 comprises a controller for controlling operation of the room UV decontamination system and UV decontamination hardware, which in this example includes at least one UV lamp, for example a UVC-radiating tube. The UV lamp is protected by the body and by a flap 1530 which can selectively cover the lamp.

The flap 1530, in this example is a hinged flap connected to a motor (not shown) operated by the controller to cause the flap 1530 to open outwards and expose the UV lamp to the room and to close back onto the body to shield the room from the UV lamp. When the controller initiates a decontamination operation, the controller, that is connected to the motor in this example electrically to provide power to the motor to cause it to operate in one direction to open the flap 1530 and in the other direction to close it, causes the flap to open. When the controller interrupts or otherwise terminates a decontamination operation, the controller causes the flap 1530 to close, here by providing controlling signals to the motor to cause this, such that the room is shielded from the UV decontamination hardware and thus irradiation of the room by the UV lamp is prevented. In this manner the flap 1530 serves as a redundant safety measure (secondary to disabling the UV decontamination hardware) to ensure that the room is not irradiated when safe conditions do not exist.

In this example, the body 1505 defines an enclosed space within which the UV decontamination hardware is contained. Like in the example of FIG. 6, a ventilation system can cause air flow within the body 1505. In the example shown here, the ventilation system comprises a motorized fan 1535 located in fluid communication with (in this case in front of) a window 1540 at one longitudinal end of the body 1505. Another window (not visible in FIG. 12) located at the other longitudinal end of the body 1505 allows the air drawn in to escape. The fan 1535 is powered by an electromotor controlled by the controller. In this example, the controller is in electric communication with the fan's electromotor and selectively provides power to the electromotor to cause it to turn, however the controller can be configured to communicate in other manners with the electromotor to control its operation.

The ventilation system may therefore cool the UV decontamination hardware while in use. The ventilation system may also be used to decontaminate air. In use, when the room UV decontamination system 1500 is performing a room decontamination operation, the ventilation system causes the air exposed to the UV decontamination hardware to circulate thereby exposing airborne pathogens to UV radiation. In one example however, when room UV decontamination system 1500 is not used to perform a room decontamination operation whereby surfaces in the room are exposed to UV radiation, the room UV decontamination system 1500 may be used to perform an air decontamination operation. In one example of an air decontamination operation, controller causes the flap 1530 to remain shut, while causing the UV decontamination hardware to irradiate the interior of the body 1505. Simultaneously, the controller causes the fan 1535 to run so as to cause the flow of air within the body 1505 to irradiate the passing air within the body 1505 and thereby cause the irradiation of airborne pathogens. The interior of the body 1505 around the UV decontamination hardware, including the inside of the flap 1530 may be made of UV reflective material to ensure complete exposure of the passing air. In order to prevent UV radiation leaking, a system of internal shades or walls causing turns in the air path inside the body 1505 may be placed on both sides of the UV decontamination hardware such that there is no straight-line path from the UV lamp to the windows through which the UV rays could travel. In order to limit reflected UV leakage the internal shades or walls, as well as the rest of the body 1505 near the windows may be made of or coated with UV-absorbent material.

In another embodiment, the entire ventilation system may be enclosed within the body 1505 behind the flap 1530 such that no windows expose connect interior of the body 1505 to the room when the flap 1530 is closed. In one such example the fan 1535 is simply placed near one end of the UV decontamination hardware in the open cavity of the body 1505 behind the flap 1530. In this embodiment, the system 1500 does not provide air decontamination operations as separate from room decontamination operations.

Like in previous examples, the system 1500 comprises condition sensing hardware. In this particular example, the condition sensing hardware comprises a door sensor 1545 and a presence detector 1510.

Like in the example of FIG. 1, the door sensor 1545 is a sensor for detecting, when installed, the use of a door in relation to which it is installed. The door sensor 1545 generates an output in the form of sensor data indicative of the door use. To this effect, the door sensor 1545 may detect door opening or closing or both, and generate sensor data indicative of the detected action. In the present example, the door sensor 1545 is a magnetic sensor like the one of FIG. 1. It may be installed on a door, such as the door 1550 shown in FIG. 12. Like in the example of FIG. 1, the door sensor 1545 of this example is a reed and magnet sensor that outputs a condition of open or closed circuit depending on whether the door is opened or closed. The door sensor 1545 can be provided as part of the system 1500 ready to be installed on a door. For practicality of installation, the door sensor 1545 is provided separately from the body 1505 of the system 1500, connected thereto, and to the controller, by a wire such that the controller may receive as input the output of the door sensor 1545. The door sensor 1545 of this example is suited for installing in relation to a door such that the door sensor can be used to detect the status of the door, e.g. the open and closed states of the door. Since the door sensor 1545 of this example is magnetic, the door sensor comprises its two portions, a reed which can be affixed, e.g. nailed, into the wall or doorframe near the door and a magnet which can be affixed, e.g. nailed, into the door at a position where, when the door is closed, the magnet comes sufficiently close to the reed to effect the sensing. In this example, the magnet may be apart from the body 1505 and connected, for example by an electrical loop 1546 which is made into an opened or closed circuit by the reed depending on the state of the door. Of course, this door sensor 1545 is exemplary only and other kinds of door sensors may be used such as optical sensors (e.g. reflective device that outputs light and detects the output light reflected by the door when it is closed).

Le presence detector 1510 is hardware suitable for detecting a presence in proximity of the door, and preferably in the room in general, when the system 1500 is installed in a room. In this example, the presence detector comprises two presence sensors 1515, 1520, which in this particular embodiment are passive infrared (PIR) sensors capable of detecting the heat radiated by living bodies, such as humans or animals. Advantageously, PIR sensors may thus detect presence of a human even in the absence of motion. Such sensors may therefore avoid an accidental lack of detection if a human is immobile in the room, for example if the human is passed out, or simply lying or sitting still.

In the present example the system 1500 is configured to be installed in a room over the door to be monitored. The presence detector 1510 is configured such that when installed it can detect a presence in proximity to the door. If a door is opened by a human, a human presence exists in proximity to the door. For example, for a typical hinged door, an arm will be touching the door to push or pull the door. An arm in contact with the door may be considered a presence in proximity to the door and the presence detector 1510 may be configured to detect such a presence by being oriented such that when installed the pathway of the door, and therefore the arm, is in view of one of the presence sensors 1515, 1520. Not all doors are hinged and not all doors require manual actuation. For example an automated sliding door may open without needing an arm to push or pull it across its path. However, if a door is opened with the purpose of accessing a room behind it, a being will cross the threshold of the door, thus providing a presence in proximity to the door. The presence detector 1510 may be configured to detect such a presence by being oriented such that when installed the threshold of the door, or the area adjacent the threshold is exposed to the presence sensors 1515, 1520 such that it may detect a body crossing the threshold of the door. Finally, in a small room such as a single occupant bathroom, the area inside the room may be in proximity to the door, thus the presence detector 1510, if configured to detect a presence inside the room when installed, may be configured to detect a presence in proximity to the door by being configured to detect a presence inside the room.

In the present example, the presence sensor 1515 has a field of view that covers the pathway of a door when the body 1505 is installed over the door. It will be appreciated that to allow the system 1505 to suit a different room configuration, the presence detector 1510 may be provided outside the body 1505, like the door sensor 1545, and connected to the controller by a suitable connection, for example an electrical connection or, if independently powered, a Bluetooth connection or the like. Staying with the illustrated example, when the system 1505 is installed in a room over a door, the presence sensor 1515 is oriented such as to be able to sense a presence in the pathway of the door, crossing the threshold of the door, and generally inside the room near the door. Presence sensor 1520 is oriented towards the interior of the room so as to ensure sensor coverage of the room. In the present embodiment, presence sensing by any of the presence sensors 1515, 1520 is treated as a positive detection of a presence. Presence detector 1510 is in communication with the controller to provide the controller an output indicative of detected presences. In practice, in this particular example, the presence sensors 1515, 1520 comprise a pyroelectric sensor and circuitry that outputs a voltage "high" (e.g. 3.3V) across an output whenever a presence is sensed. These outputs are provided to the controller which interprets a voltage high from either one as a detection of a presence by the presence detector 1510. It will be noted that the presence detector 1510 provided in this example may be used in rooms with automatic and/or sliding doors since it will detect the presence of a body crossing the door threshold. In alternate embodiments, if desired, a presence sensor of the presence detector may be installed outside the room in which the system 1500 is to be used to detect bodies in proximity to the other side of the door before the door is even opened.

The use of dual presence sensors allows for a certain measure of safety redundancy in case one presence sensor is malfunctioning due to, e.g. parts failure or tampering. In the present design, the presence sensor 1515 is located, when installed, over the opening side of the door and therefore is more easily accessible to a person attempting to obfuscate the sensor's view of the room, e.g. during opening of the door. The other presence sensor 1520 is located on the opposite side and cannot readily be accessed without first entering the room and coming into view of the presence sensor 1520. Thus the use of dual sensor allows for a safe and hard-to-tamper configuration. In alternate embodiments, however, a single sensor may be used to monitor the room and/or the area proximate the door.

While in the example provided here the presence detector 1510 comprises PIR sensors, it will be appreciated that other forms of presence sensors may be used. For example motion detectors that rely on visual interpretation of a field of vision, in visible light or in infrared light may be used alongside, or instead of PIR sensors. If using active infrared motion detectors which emit infrared light, care must be taken to select motion detectors operating on a wavelength that will not interfere with the PIR sensor's ability to detect human bodies if one wishes to combine the two most effectively. Motion may itself be an indicator of presence. In general, motion sensed within the room may be used by the controller as an indicator that there is a presence in the room. Likewise, motion of the door, with or without a human's heat signature detected may be interpreted, in some embodiments, by the controller as a presence in proximity to the door. The presence detector may be configured for detecting the door itself during opening or closing, for use by the controller in confirming that the presence detector can indeed detect, e.g., motion. Although motion may be caused by non-human factors such as paper picked up by a draft current, erring on the side of detection allows the system to avoid false negatives and false presumptions that the room is empty when in fact it isn't. Moreover, as described herein, presence detection may be used to confirm that the presence detector is functioning properly. In this respect the detection of even a non-human presence may allow the controller to ascertain that the detector functions properly insofar as it is capable of detecting presence.

Although in the present example the system 1500 comprises only one door sensor 1545, additional door sensors may be provided to accommodate additional doors to the room. Each additional door sensor may be connected to the controller in the like the door sensor 1545. In examples where the system 1500 is configured for installation in a room with multiple doors, the presence detector 1510 may be configured to detect a presence in proximity to each door. To this end, the presence sensors (here 1515 and 1520) may be configured to be, when installed in view of the multiple doors or additional presence sensors may be provided in a configuration that, when installed, can detect a presence in proximity to the additional doors.

Operation of the system 1500 will now be described in relation to the embodiment described herein. As has been described, decontaminating rooms using UV radiation poses a significant hazard to humans if present at the time of the decontamination. Therefore it is particularly important to ensure the non-occupancy of the room prior to commencing decontamination operations. In this respect, presence detectors, particularly the kind capable of detecting immobile humans, are very useful since they can generally reliably ascertain whether a room is free of humans. However, if such detectors are to be relied upon for ensuring the non-occupancy of a room, it is crucial that they work properly and are free of defects and tampering. The building security industry offers a number of tamper-proofing techniques for preventing or detecting tampering of sensors, including PIR sensors. While these techniques may be good enough for the purpose of security, to prevent active harm being done to humans it is necessary to have security not only cannot itself be tampered with but also that will detect non-tamper-related failures in the sensing apparatuses. Advantageously, while false positive detections can be a serious problem in the security setting, leading to expensive interventions, in the room sanitation field, a false positive merely leads to, at worst, a skipped cleaning cycle.

In order to ascertain that safe conditions for decontamination exist in the room, the system 1500 performs a confirmation that the presence detector 1510 is functioning properly. The confirmation allows not only to test that the presence detector 1501 is actually capable of detecting a presence but also that it is, e.g., not occluded and installed properly. It is crucial that PIR sensors work properly if we are actually going to use them to determine safe conditions.

Figure 13:
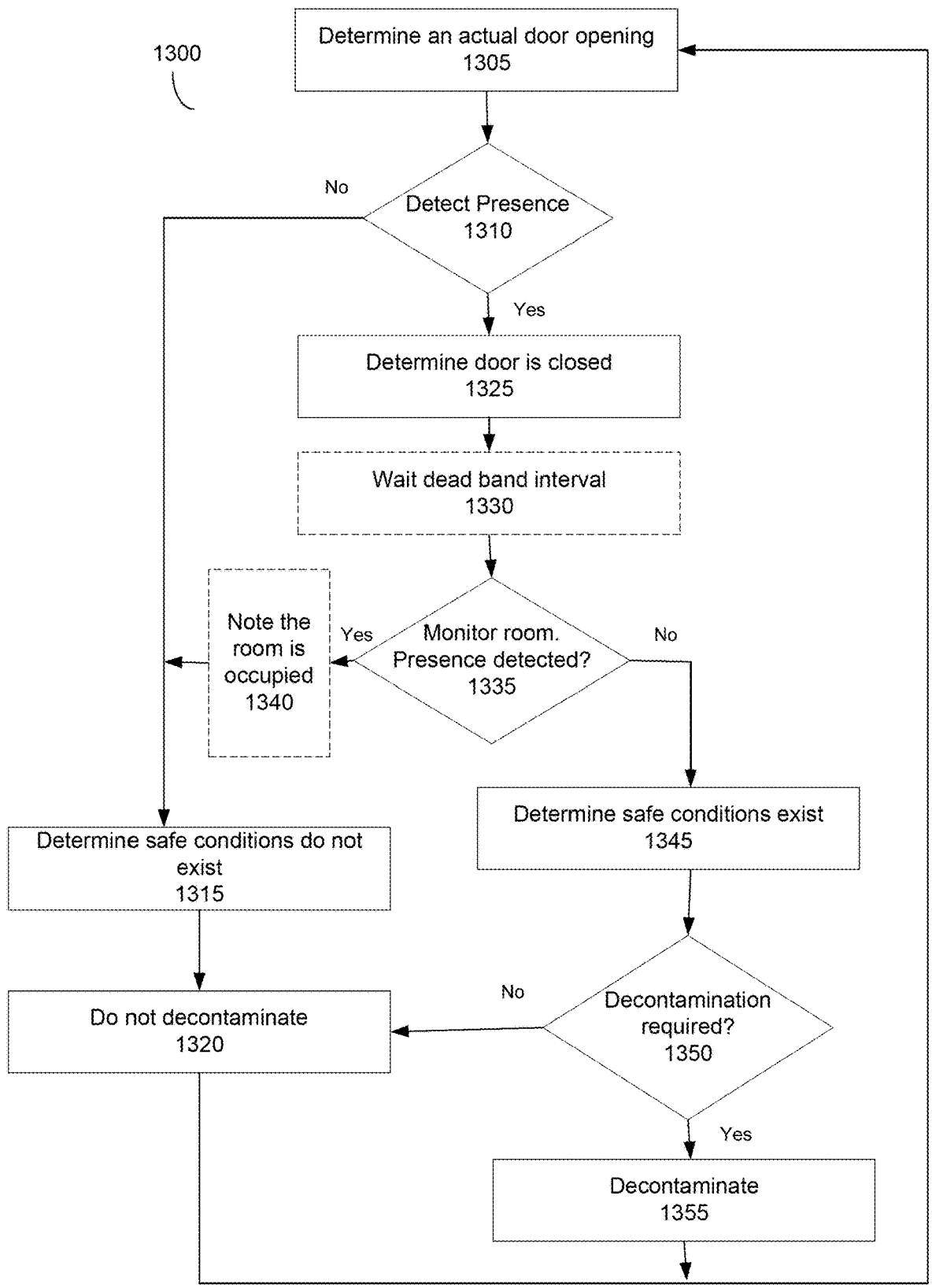
FIG. 13 illustrates a flowchart of some of the operations of the system of FIG. 12.

FIG. 13 illustrates a flowchart 1300 of some of the system 1500's controller's operations. The determination of whether safe conditions for contamination exist may be triggered by a door use, particularly an opening and/or closing of the door. Since safe conditions exist when the room is free of humans, and presumably the room becomes free of humans when the last human in the room leaves through the door (here assumed to be singular for simplicity), a detected door use is a suitable trigger to the controller to trigger the determination.

In this example the system 1500 is already installed, as illustrated in FIG. 12, in a room with a door. At step 1305, the door opens and this is sensed by the door sensor 1545 which responds by generating an output indicative that the door is open, in this example, by causing an open circuit in the loop 1546. The loop 1546 is connected to the controller, which determines, on the basis of the output, that there has been an actual door opening. In this embodiment, when the controller receives the door sensor 1545's output indicative of the door opening, the controller performs a determination of whether there was an actual door opening, which involves determining if the door opening satisfies a certain requirement, in this case a minimum duration. To this end, the controller comprises a timer for counting a preset open-door period of time to ascertain whether the door has been opened for the open-door period of time before determining that an actual door opening has occurred. In this example, the timer comprises a counter and logic for incrementing the counter at set intervals as well as logic for comparing the counter value to a preset value which is attained, according to the incrementing at or after the open-door period of time. In a hardware embodiment, this may be implemented by a simple clock cycle-driven counter and a comparator. During the timing, if the door sensor 1545 indicates that the doors has now closed again, by generating an output indicative of the door being closed, for example, then controller assumes that no actual door opening has occurred and returns to the state it was in prior to receiving the indication of door opening form the door sensor 1545. The open-door period of time may be set, for example, to be too short for a person to actually cross the door. Thus the door is only opened very quickly and closed again, as may happen, for example if the door is merely nudged by a passer-by, or if someone opens the door to a bathroom and realizes that it is occupied, the controller will not determine that an actual door opening has occurred and thus will begin a determination of whether safe conditions of decontamination exist in the room. It will be noted that in other embodiment the timing step may be omitted. The controller may, for example, consider any door opening an actual door opening.

However, if the conditions for an actual door opening are satisfied, in this example by the controller confirming from the door sensor 1545's output that the door has been opened for at least the door-open period of time, the controller then determines whether the door opening coincides with a detected presence at step 1310. In this embodiment, the controller will never initiate a decontamination operation if the presence detector 1510 detects a presence in the room (or if the door is open), and will interrupt any decontamination operation in progress if a presence is detected in the room (or if the door is opened). Thus there is no danger, if the presence detector 1510 is emitting false positives, that a person will accidentally be irradiated. However, if the presence detector 1510 is not functioning properly in that it fails or would fail to detect a presence where there is one, without checking that the presence detector 1510 functions properly there would be a danger that a person may be accidentally irradiated. To this end the system 1500 under the control of the controller performs a verification that the presence detector 1510 does detect a presence at a moment when it can be assumed a presence should be detected, that is during the operation of the door. Indeed, if someone is entering the room through the door, this person must have a presence in proximity of the door while it is opened, when the person is pushing opened the door, or at least when the person is crossing the threshold of the door into the room. Since the presence detector 1510 is configured to detect a presence in proximity to the door, it can be verified at this moment that the presence detector 1510 is functioning properly by checking that the presence detector 1510 is indeed detecting a presence in proximity of the door during a time that the door is opened. If no presence is detected during that time, it may be that the presence detector 1510 is not functioning properly and therefore it cannot be assumed that safe conditions for decontamination exist in the room, at least not on the basis of the output of the presence detector 1510. Thus the controller, having failed to confirm that the presence detector 1510 is functioning properly will not base a determination that safe conditions for decontamination exist in the room on the output of the presence detector 1510. If other means for determining safe conditions that do not require the presence detector 1510 are available to the controller, they may be used instead. However, in the present embodiment a determination of safe conditions requires determining on the basis of the presence detector 1510 that there is nobody in the room. Thus if the controller cannot confirm that the presence detector 1510 is functioning properly, it will simply determine that safe conditions for contamination do not exist in the room, and it will initiate no decontamination operation.

Thus at step 1310, the controller determines on the basis of the detector output whether the actual opening of the door coincides with a detected presence. In particular, once the controller determines an actual door opening, the controller monitors the output of the presence detector 1510 to determine whether a presence is detected in proximity to the door. In one particular embodiment, any presence detected from either of the presence sensors 1515, 1520 will be treated as a detected presence in proximity to the door, since in this example bother sensors 1515, 1520 are capable of detecting a presence in proximity to the door. As mentioned herein, in this example the presence sensors 1515, 1520 output a voltage high upon sensing a presence. The controller combines these outputs in an OR function and monitors the output of this function to determine whether a presence has been detected coinciding with the door opening. If the controller determines, on the basis of the presence detector 1510's output that a presence is detected coinciding with the door opening, then the controller confirms that the presence detector 1510 is functioning properly.

In another embodiment, particular sensor is dedicated to detecting a presence in proximity to the door and the controller must determine that that particular sensor, on the basis of the particular output of that particular sensor, has sensed a presence in proximity to the door in order to confirm that the presence detector is functioning properly.

In the present embodiment, the controller monitors the presence detector 1510 for the duration of the door's opening as detected on the basis of the output of the door sensor 1545. Thus the controller monitors the output of the presence detector at least as of when the controller determines an actual door opening, and at least until the controller determines a presence is detected in proximity to the door or until the controller determines that the door is closed. If a presence is detected before the door is determined to be closed, the controller confirms that the presence detector 1510 is functioning properly. In alternative embodiments, coincidence with the actual door opening may be determined differently. For example, the controller may comprise a timer, similar to the open-door timer that counts down a preset door-monitoring period of time. This may be useful where the door sensor is configured in such a way that it might signify a door closing before the door is actually closed. In such a case, the preset door-monitoring period may be set to a maximum amount of time it is expected to take a person to cross the threshold of the door. The door-monitoring period of time may be set as the definitive amount of time during which a presence must be determined in order to confirm that the presence detector 1510 functions properly, or it may be, for example, a minimum amount of time in which, if a presence is determined, the controller will confirm proper functioning of the presence detector 1510, but the controller in any case continues to monitor the output of presence detector 1510 for the purpose of confirming its proper functioning until the door closes. Similarly, by using timers, the door-monitoring start and finish may be set as a function of the time at which the controller determines actual opening of the door, for example starting a second after the door has been opened, and continuing until a second after the door has been closed. This may be useful in the case of automatic doors when a person is not expected to penetrate the room immediately when the door opens, and when the door sensor is an input from the automatic door that cannot safely be relied upon to be perfectly accurate.

In yet another variant where multiple presence sensors are used, as is the case in the example of FIG. 12, determining that the presence detector 1510 is functioning properly may involve confirming the sensing done by one sensor with that of another. For example, if presence sensors 1515 and 1520 are configured to both detect a presence in proximity to the door, the controller may not confirm that the presence detector 1510 is functioning properly unless both sensors provide an output that correlates with one another, for example if both sensors provide an output indicative of a presence detected in proximity to the door. This way additional redundant safety may be built into the system 1500 such that the failing of a single presence sensor prevents the determination of safe conditions and therefore prevents decontamination operations from being initiated.

Optionally, the controller may be provided with a logging system of the type described herein which may generate logging data indicative of a failure by the controller to confirm the proper functioning of the presence detector, and/or generate alerts on this basis.

Now as mentioned herein, if the controller does not, during door-monitoring, confirm that the presence detector 1510 is functioning properly, the controller at step 1315 determines that safe conditions for decontamination do not exist and does not initiate decontamination operations (1320).

In the present example, the controller continues to detect presence (1310) until the controller determines on the basis of the door sensor 1545's output that the door has been shut at step 1325. At this point, in some embodiments the controller may determine that safe conditions for decontamination exist and may then initiate a decontamination operation. In this embodiment, however, in order to be doubly sure that the room in which the system 1500 is installed is indeed empty, the controller will then perform a room monitoring operation for a certain amount of time using the presence detector 1510.

The controller determines that the door is closed based on the door sensor 1545's output. The controller also monitors the output of the presence detector 1510 and determines on the basis of this output whether a presence is detected. On the basis of the closed status of the door and the lack of presence detection, the controller determines that safe conditions for decontamination exist.

Due to their physical nature, PIR sensors typically hold a presence signal for a certain period of time after the presence they have detected has disappeared. For this reason, at step 1330, the controller will wait a certain dead band period to allow the PIR sensor to cease outputting an output resulting from the presence they detected while the door was opened. Otherwise, if the door had been opened because a person was leaving the room, immediately after the door shuts the PIR sensors may still be outputting an output indicative of a sensed presence even though there is no longer a presence to detect. Thus the controller is provided with a timer, e.g. similarly to the timer described above and reusing logic used for other timers if suitable, to count down a particular dead band period, in this example three seconds.

After the dead band period has expired (or immediately, if no dead band period is used), the controller at 1335 monitors the room to detect any indication that safe conditions do not exist. In the present embodiment, the controller monitors the output of the presence detector 1510 in order to determine whether a presence is detected. If a presence is detected during the room monitoring, the controller immediately determines that safe conditions for decontamination do not exist, at 1315, because there is a presence, possibly a person, in the room. Optionally, the controller may also note that the room is occupied at 1340, for use in conjunction with the techniques described above, or for use in determining whether a decontamination operation is necessary, as described herein below. To this end, the controller may comprise a memory suitable for storing log data as described above or simply a flag or counter which is flagged/incremented when the room has been used.

Preferably, the controller also continuously monitors the output of the door sensor 1545 at step 1335. If at any time the door is opened, the controller determines that safe conditions for decontamination do not exist (1315) and does not decontaminate the room (or ceases any decontamination in progress) and returns to step 1305. Preferably this occurs regardless of where in the event flow the controller is when the door is opened. Door openings that are not actual door openings (e.g. that do not satisfy the minimum open-door period of time) could be treated as non-events to ignore, however in order to avoid any leaking of UV radiation outside the room, the controller in this embodiment considers even short (non-"actual") door openings to signify a danger. As such, the controller is configured to determines, upon the very first detection of a door opening of any length that safe conditions for decontamination do not exist (1315), does not initiate and immediately interrupts any ongoing decontamination operation (1320) and returns to step 1305 whereupon it then ascertains whether the door opening is an "actual" door opening.

Room monitoring prior to determining safe conditions for decontamination may be performed for a certain period, which in this example is a preset room monitoring period of 15 minutes. To this end, the controller is provided with a timer to count out the preset room monitoring period of time. In alternative embodiments, the room monitoring period may be conditional, e.g. a function of the frequency of use of the room.

Upon completion of the room monitoring period, if no presence was determined by the controller and no door opening was detected, the controller then at step 1345 determines that safe conditions for decontamination exist in the room. At this point, the controller may initiate a decontamination operation 1355. Preferably, even after safe conditions have been determined, and throughout the decontamination operation, the controller continues to monitor the output of the condition sensing hardware, in this example the presence detector 1510 and the door sensor 1545 to immediately determine that safe conditions for decontamination do not exist, and not initiate/interrupt any decontamination operation. In certain examples where the presence sensing hardware is interfered with by the decontamination equipment the controller may rely uniquely on the non-interfered-with hardware, e.g. the door sensor (but optionally other hardware such as the user input interface described above) during decontamination operation.

Upon determining safe conditions, the controller may automatically initiate a decontamination operation. As described further herein, the controller may also further verify, at step 1350, whether a decontamination operation is required. If no decontamination is required, it does not initiate decontamination. If a decontamination operation is required (or, in other examples, simple if safe conditions exist), the controller at step 1355 initiates decontamination operation. Since this may be an interruptible decontamination operation, the controller may also verify whether the decontamination operation is successfully completed, maintaining the requirement for decontamination if it isn't.

Advantageously, the system 1500 not only allows for reliable determination of safe conditions for decontamination but also is also configured to ascertain when decontamination operations are necessary. In particular, the controller is configured to determine on the basis of the condition sensing hardware's output when the room is occupied and to maintain in memory an indication that the room has been used. It then uses this knowledge to make a decision as to whether a decontamination operation is required.

As described herein, the controller may determine whether decontamination is required on the basis of, for example, a regular schedule or an amount of time since the last successful decontamination operation has been effected. In addition, the controller may use historical data, not only on past decontamination operation but also on other conditions as determined from the output of condition sensing hardware, to determine whether a decontamination operation is required. In the present example, the controller of the system 1500 generates and stores data indicative of occupancy of the room in order to generate historical room utilisation data, which it then uses to determine whether a decontamination operation is required.

Figure 14:
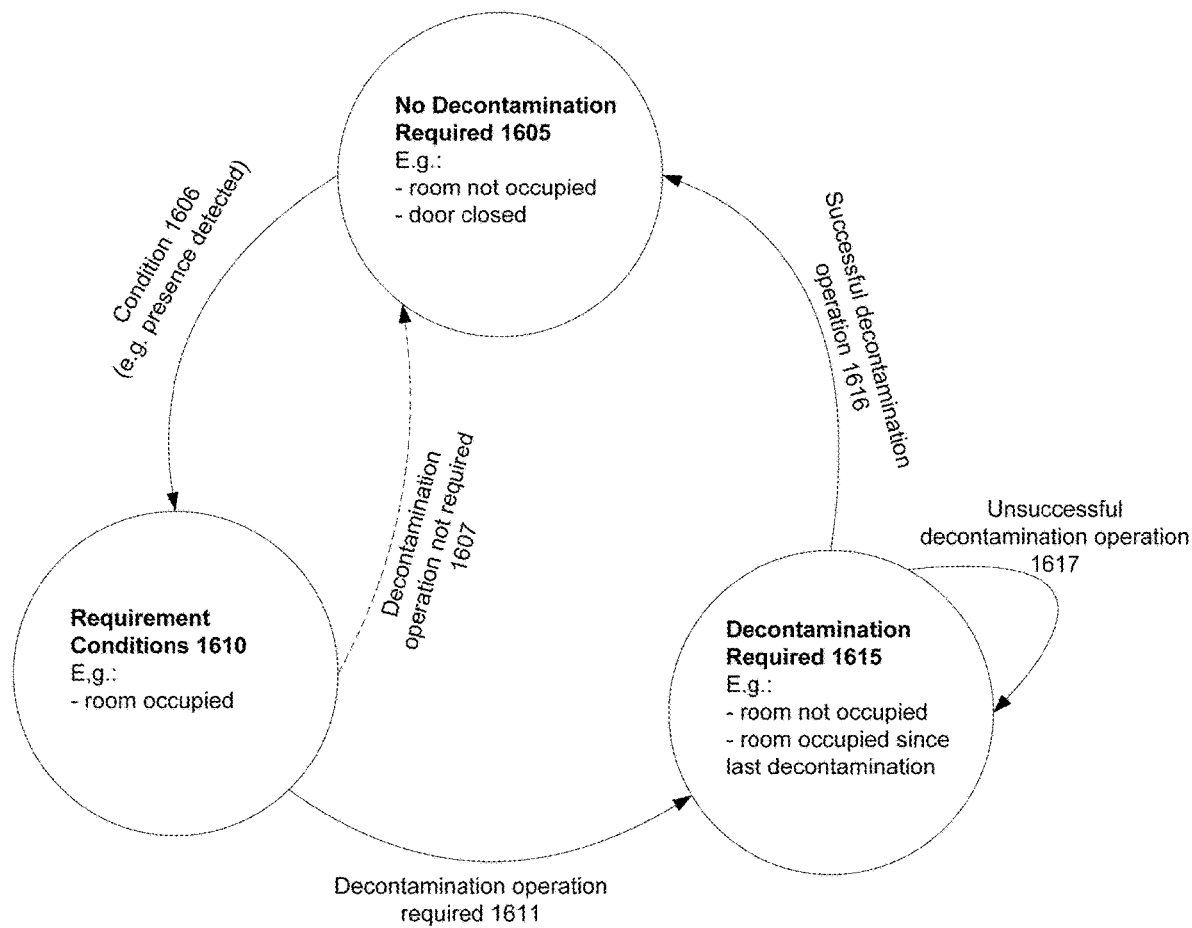
FIG. 14 shows a state machine diagram showing and exemplary process of determining that decontamination operations are required.

FIG. 14 shows a state machine diagram showing the process of determining that decontamination operations are required. At state 1605, no decontamination is needed as determined by the controller, and in this example the room is unoccupied. Taking this as a starting point, the controller determines that a decontamination operation is required on the basis of the output of the condition sensing hardware. In particular, the controller verifies whether the output of the condition sensing hardware corresponds to a particular decontamination requirement condition. In this example, the condition is that the room has been occupied since the last decontamination operation.

When the controller determines at 1606 room occupancy on the basis of the condition sensing hardware's output, the occupied state 1610. In one example, the controller may determine occupancy of the room when the controller determines that safe conditions for decontamination do not exist. Other criteria, however, may be used. As described in relation to step 1340 of FIG. 13, the controller of this example determines room occupancy on the basis of the presence detector 1510's output. While the controller may, for example, determine that safe conditions for decontamination do not exist whenever the door is opened, in the example above the controller distinguishes between a transient door opening and an actual door opening, wherein a presence is detected in proximity of the door. In the present example, occupancy is determined on the basis of the output of the presence detector only 1510. If the door sensor 1545 indicates that the door was opened and closed rapidly and no presence was detected, while safe conditions for decontamination may not exist during the time that the door was opened, and possibly thereafter (depending on the manner in which the controller establishes safe conditions for decontamination), the controller of the present example will only consider the room to be occupied 1610 if the presence detector 1510 notes the presence of a person in the room. Other manners of determining occupancy may be used.

The controller accesses a memory to store historical condition data, in this example historical use data. In particular, it stores an indication of conditions used for requiring a decontamination have been met. In one example, the controller determines that decontamination is required when the room has been occupied since the last decontamination operation. To this end, the controller has access to a memory flag which may be a Boolean variable that is set when the controller has determined, at step 1340, that the room is occupied. In other examples, the conditions for requiring a room decontamination may be different. For example in one variant, the controller determines that decontamination operation is required after the room has been occupied 5 times since the last decontamination operation. In this case, the controller may increment a conditions counter in memory whenever the controller detects a new room occupancy.

Once the controller determines that the room is no longer used (or more generally that the condition with which it determines the requirement of decontamination is no longer present) it transitions to another state. If the condition was not on its own sufficient for requiring a decontamination operation, and the decontamination operation is not yet required, the controller returns to state 1605 where no decontamination operation is required. This may be, for example, the case when the controller only determines decontamination is required if at least 5 room occupancies have occurred since the last decontamination operation. Thus the controller performs a determination of whether a decontamination operation is required, for example by comparing the value of the conditions counter with a, e.g. preset, threshold. If the controller determines that a decontamination operation is not required, 1607, it returns to state 1605.

In the present example, a single room occupancy is considered by the controller to create a requirement for a decontamination operation. Thus, the controller performs the determination at 1611 that the conditions for a requirement of decontamination have been met and enters a state 1615 where it has determined that a decontamination operation is required. The controller will then initiate a decontamination operation at least in part on the basis of the requirement it has determined. In the present example, the controller also initiates a decontamination operation on the basis of the determination of safe conditions for decontamination. Therefore the controller with remain at state 1615 until safe conditions for decontamination have been determined.

The determination at 1611 that a decontamination operation is required is based in this example uniquely on past condition data, and in particular on past room occupancy data. However, the controller may also base the determination of the requirement on other factors, such as chronological factors, such as scheduled decontamination operations or a minimum frequency of decontamination operation. For example, the controller may be configured to determine that a decontamination operation is required when the soonest of either five occupancies or a maximum time period (e.g. 1 day) since the last decontamination operation has occurred. In another example, the controller may be configured to determine that decontamination is require on a scheduled basis and on a basis of historical use (e.g. every day at 9:00—or as soon as possible thereafter—but also every time the room has been occupied). Thus at 1611, the controller ascertains that conditions data (e.g. historical room occupancy data) and, optionally, other data (e.g. chronological data such as a schedule of decontamination) that a decontamination operation is required.

On the basis of the determination that a decontamination operation is required, the controller performs a decontamination operation at 1616. The controller may account for incomplete decontamination operations, and may deal with them as described herein. In the present example, if the decontamination operation is interrupted the controller, at 1717, continues to consider that a decontamination operation is required.

At 1616, the controller successfully performs a decontamination operation. As such the conditions data, in this example the historical occupancy data, is reset by the controller. In the present example, the controller is configured to determine that decontamination is required every time the room has been occupied, and a single Boolean flag is used to determine that the decontamination requirement conditions have been met; the controller resets this flag to indicate that no decontamination operations are required. Where additional data is used in the determination of decontamination requirements, this additional data may be reset to a default value. For example where decontamination is required after five room occupancies as counted by the controller using a counter, the count may be reset to 0 upon the completion of a successful decontamination operation.

In the present embodiment, the system 1500 is suitable for a single room, and the controller is integral to the system 1500, more particularly is located within the body 1505. It is to be understood that the particular embodiment shown here is for the purpose of illustrating an example. In alternative embodiments, for example where a room is too big, or too complex in geometry to allow for decontamination from a single location the system 1500 may include several bodies having UV decontamination hardware, to perform decontamination from different locations within a room the system may be installed in. Likewise the presence detector 1510 may be distributed over a plurality of bodies and/or may include external sensors for positioning in areas of a room of which the body(ies), if installed in the room at a particular location, would not provide a view. For example extra presence sensors may be provided for installation in/over bathroom stalls, which extra presence sensors may be in communication with the controller and used thereby as described herein.

A single controller may be configured to control more than one system 1500. In one example where the functionality of the controller is provided by software running on a server, a network of systems 1500 may be installed in, e.g. a building (for example throughout the bathrooms of a hospital), each of which being in communication, e.g. through a local area network, with the server which implements the controller functionality for each of the systems 1500 in the network.

The above description has been provided for the purpose of illustrating, not limiting the invention which is defined by the appended claims.

What is claimed is:

1. A room decontamination apparatus comprising:
    a light sensor responsive to activation of a light;
    a light source actuator operable to activate and deactivate said light;
    a door sensor responsive to position of a door;
    decontamination hardware; and
    a controller in signal communication between the decontamination hardware, the light sensor, the door sensor and the light source actuator, said controller configured to automatically deactivate the light through the light source actuator in response to at least an activity of the door sensor and activate the decontamination hardware for a predetermined disinfection treatment time in response to the light sensor and the door sensor if the light has remained off and the door has remained closed for a predetermined safety time period of at least about 15 minutes, wherein the controller is configured to automatically deactivate the decontamination hardware during said predetermined disinfection treatment time in response to the door sensor if the door is opened or in response to the light sensor if the light is turned on.

2. The room decontamination apparatus of claim 1, the decontamination hardware comprising an ultraviolet (UV) emitter.

3. The room decontamination apparatus of claim 1, wherein the controller is configured to activate the decontamination hardware in response to the sensors detecting that the light is off and then the door is closed.

4. The room decontamination apparatus of claim 1, wherein the door sensor is configured for installation in relation to a door to a decontamination room and to generate an output indicative of the opening or closing of said door.

5. The room decontamination apparatus of claim 1, the sensors configured for detecting a non-presence of a being and generating an output indicative of a detected non-presence, the controller being configured for performing a determination that safe conditions exist for the decontamination operation and initiating the decontamination operation based on the determination that safe conditions exist and confirmation that the sensors are functioning properly.

6. The room decontamination apparatus of claim 1, further comprising at least one of a motion sensor or a temperature-source sensor, wherein the controller is further responsive to the at least one motion sensor or temperature-source sensor.

7. The room decontamination apparatus of claim 1, further comprising:
   a memory device for storing an historical decontamination operations log; and
   a data interface for transmitting at least a portion of the decontamination operations log to a remote device,
   wherein the historical decontamination operations log comprises decontamination operation data representative of decontamination operations initiated by the room decontamination apparatus controller, including the time at which each decontamination operation occurred.

8. The room decontamination apparatus of claim 1 wherein said controller comprises a timer configured to wait a predetermined safe period after the light is off and the door is closed prior to activation of the decontamination hardware.

9. The room decontamination apparatus of claim 1 wherein at least one of the door sensor or the light sensor or the decontamination hardware is in wireless signal communication with the controller.

10. A self-decontaminating institutional lavatory comprising:
   at least one of a sink, shower or toilet;
   a light;
   a door;
   a light sensor responsive to activation of the light;
   a light source actuator operable to activate and deactivate said light;
   a door sensor responsive to position of the door;
   decontamination hardware; and
   a controller in signal communication between the decontamination hardware, the light sensor, the door sensor and the light source actuator, said controller configured to automatically deactivate the light through the light source actuator in response to at least an activity of the door sensor and activate the decontamination hardware for a predetermined disinfection treatment time in response to the light sensor and the door sensor if the light has remained off and the door has remained closed for a predetermined safety time period of at least about 15 minutes,
   wherein the controller is configured to automatically deactivate the decontamination hardware during said predetermined disinfection treatment time in response to the door sensor if the door is opened or in response to the light sensor if the light is turned on.

11. The self-decontaminating institutional lavatory of claim 10 wherein the light sensor is further responsive to deactivation of the light and the controller is further configured to activate the decontamination hardware based on confirmation that the sensors are functioning properly by determining based on the light sensor an activation of the light and determining based on the door sensor an opening of the door, followed by determining based on the light sensor a deactivation of the light and determining based on the door sensor a closing of the door.

12. A method for decontaminating a room comprising:
   monitoring a light;
   monitoring a door;
   automatically deactivating the light in response to at least an activity of the door;
   detecting a safe condition in response to the monitored light and the monitored door if the light has remained off and the door has remained closed for a predetermined safety time period of at least about 15 minutes;
   automatically activating decontamination hardware for a predetermined disinfection treatment time based on the detected safe condition while the light is off and the door is closed, and automatically deactivate the decontamination hardware during said predetermined disinfection treatment time in response to the door sensor if the door is opened or in response to the light sensor if the light is turned on.

13. The room decontamination method of claim 12, activating the decontamination hardware comprising activating an ultraviolet (UV) emitter.

14. The room decontamination method of claim 12, further comprising deactivating the decontamination hardware in response to detecting a presence if the light is on or the door is open.

15. The room decontamination method of claim 12, further comprising activating the decontamination hardware if the light is off when the door is closed.

16. The room decontamination method of claim 12, further comprising monitoring a door switch in relation to the door to a decontamination room and detecting a status of the door to generate an output indicative of the status of the door.

17. The room decontamination method of claim 12, detecting a safe condition comprising detecting a non-presence of a being and generating an output indicative of a detected non-presence, and performing a determination that safe conditions exist for the decontamination operation and initiating the decontamination operation based on the determination that safe conditions exist and confirmation that the detection of non-presence is not erroneous.

18. The room decontamination method of claim 12, further comprising at least one of sensing motion or sensing a temperature source, wherein detecting a safe condition is further responsive to the sensed motion or sensed temperature source.

19. The room decontamination method of claim 12, further comprising:
   storing in a memory device an historical decontamination operations log and transmitting at least a portion of the decontamination operations log through a data interface to a remote device,
   wherein the historical decontamination operations log comprises decontamination operation data representative of decontamination operations initiated by the method for decontaminating a room, including the time at which each decontamination operation occurred.

20. The room decontamination method of claim 12, further comprising automatically closing the door after each opening.

\* \* \* \* \*